(12) United States Patent
Okano et al.

(10) Patent No.: US 9,623,052 B2
(45) Date of Patent: Apr. 18, 2017

(54) METHOD FOR PRODUCING MYOCARDIAL SHEET FROM EMBRYONIC STEM CELL

(75) Inventors: Teruo Okano, Tokyo (JP); Tatsuya Shimizu, Tokyo (JP); Jun Yamashita, Kyoto (JP); Hidetoshi Masumoto, Kyoto (JP)

(73) Assignees: Tokyo Women's Medical University, Tokyo (JP); Kyoto University, Kyoto (JP)

( * ) Notice: Subject to any disclaimer, the term of this patent is extended or adjusted under 35 U.S.C. 154(b) by 203 days.

(21) Appl. No.: 14/009,018

(22) PCT Filed: Mar. 30, 2012

(86) PCT No.: PCT/JP2012/059427
§ 371 (c)(1),
(2), (4) Date: Sep. 30, 2013

(87) PCT Pub. No.: WO2012/133945
PCT Pub. Date: Oct. 4, 2012

(65) Prior Publication Data
US 2014/0056859 A1    Feb. 27, 2014

(30) Foreign Application Priority Data

Mar. 30, 2011  (JP) ................ 2011-076235

(51) Int. Cl.
| | | |
|---|---|---|
| A61K 35/34 | (2015.01) | |
| C12N 5/077 | (2010.01) | |
| C12N 5/071 | (2010.01) | |
| A61K 35/44 | (2015.01) | |
| A61K 9/70 | (2006.01) | |

(52) U.S. Cl.
CPC ............. *A61K 35/34* (2013.01); *A61K 9/70* (2013.01); *A61K 35/44* (2013.01); *C12N 5/0657* (2013.01); *C12N 5/0697* (2013.01); *C12N 2501/01* (2013.01); *C12N 2501/04* (2013.01); *C12N 2501/165* (2013.01); *C12N 2502/1329* (2013.01); *C12N 2502/1347* (2013.01); *C12N 2502/28* (2013.01); *C12N 2506/02* (2013.01)

(58) Field of Classification Search
None
See application file for complete search history.

(56) References Cited

U.S. PATENT DOCUMENTS

2004/0009566 A1    1/2004 Okano et al.

FOREIGN PATENT DOCUMENTS

| JP | 2007-528755 A | 10/2007 |
|---|---|---|
| WO | WO-02/08387 A1 | 1/2002 |
| WO | WO-2005/011524 A1 | 2/2005 |
| WO | WO 2009/118928 A1 | 10/2009 |

OTHER PUBLICATIONS

Masumoto (epub Mar. 21, 2012). Pluripotent Stem Cell-Engineered Cell Sheets Reassembled with Defined Cardiovascular Populations Ameliorate Reduction in Infarct Heart Function Through Cardiomyocyte-Mediated Neovascularization. Stem Cells, v30, p. 1196-1225.*
Stephens et al. (2009a). Physiological function and transplantation of scaffold-free and vascularized human cardiac muscle tissue. PNAS, v106(39), p. 16568-16573.*
Stephens et al. (2009a). Physiological function and transplantation of scaffold-free and vascularized human cardiac muscle tissue. PNAS, v106(39), p. 16568-16573; Supplemental Information, 5 pages.*
Stephens et al. (2009b). Scaffold-Free Human Cardiac Tissue Patch Created from Embryonic Stem Cells. Tissue Engineering Part A, v15(6), p. 1211-12222.*
Caspi et al. (2007). Tissue Engineering of Vascularized Cardiac Muscle From Human Embryonic Stem Cells. Circ. Res, v100, p. 263-272.*
Roy et al. New directions in thermoresponsive polymers. Chem Soc Rev (2013), v42, p. 7214-7243.*
Bel, A. et al. "Composite Cell Sheets: A Further Step Toward Safe and Effective Myocardial Regeneration by Cardiac Progenitors Derived From Embryonic Stem Cells", Circulation, 2010, vol. 122, pp. S118-S123.
International Search Report PCT/JP2012/059427 dated Jun. 19, 2012.
Masumoto, H. et al. "Embryonic Stem (ES) Cell-engineered Tissue Sheets with Defined Cardiac Cell Populations Ameliorate Function after Myocardial Infarction", Circulation Journal, 2011, vol. 75, No. Supp 1, p. 610.
Sekine, H. et al. "Cardiomyocyte Sheets Co-Cultured with Endothelial Cells Improve Cardiac Function of Ischemic Heart", Japan Research Promotion Society for Cardiovascular Disease, 2006, pp. 5-8.
Sekine, H. et al. "Endothelial Cell coculture Within Tissue-Engineered Cardiomyocyte Sheets Enhances Neovascularization and Improves Cardiac Function of Ischemic Hearts", Circulation, 2008, vol. 118, No. Suppl 1, pp. S145-S152.
Sekine, H. et al. "Transplantation of Cardiomyocyte Sheets Co-Cultured With Endothelial Cells for Ischemic Heart Failure", Japanese Association of Cardiovascular Pharmacology, 2009, vol. 19, p. 34. (English Translation).
Shimizu, T. et al. "Polysurgery of cell sheet grafts overocmes diffusion limits to produce thick, vascularized myocardial tissues", The FASEB Journal, 2006, vol. 20, pp. 708-710.
Shimizu, T. et al., "Cell sheet engineering for myocardial tissue reconstruction", Biomaterial, vol. 24 (2003) 2309-2316.

(Continued)

*Primary Examiner* — Scott Long
*Assistant Examiner* — Sean C Barron
(74) *Attorney, Agent, or Firm* — Foley & Lardner LLP

(57) ABSTRACT

The present invention provides a method for producing a myocardial sheet using a group of cells derived from embryonic stem cells. This method is characterized by mixing Flk/KDR positive cells, cardiomyocytes, endothelial cells, and mural cells, all derived from embryonic stem cells, and culturing the mixed cells. Furthermore, the myocardial sheet can be used as a therapeutic agent for heart diseases since VEGF is released from the sheet.

7 Claims, 15 Drawing Sheets
(11 of 15 Drawing Sheet(s) Filed in Color)

(56) References Cited

OTHER PUBLICATIONS

Yamashita, J. et al. "Flk1-positive cells derived from embryonic stem cells serve as vascular progenitors", Nature, Nov. 2, 2000, vol. 408, pp. 92-96.
Yan, P. et al. "Cyclosporin-A potently induces higly cardiogenic progenitors from embryonic stem cells", Biochemical and Biophysical Research Communications, 2009, vol. 379, pp. 115-120.
Yang, L. et al. "Human cardiovascular progenitor cells develop from a KDR+ embryonic-stem-cell-derived population", Nature, 2008, vol. 453, pp. 524-528.
Yurugi-Kobayashi, T. et al. "Adrenomedullin/Cyclic AMP Pathway Induces Notch Activation and Differentiation of Arterial Endothelial Cells from Vascular Progenitors", Arteriosclerosis, Thrombosis, and Vascular Biology, 2006, vol. 26, pp. 1977-1984.
Supplementary European Search Report dated Dec. 9, 2014, in EP 12763936.7.
Kattman et al., "Multipotent Flk-1+Cardiovascular Progenitor Cells Give Rise to the Cardiomyocyte, Endothelial, and Vascular Smooth Muscle Lineages," Developmental Cell, Nov. 2006, 11:723-732.

\* cited by examiner

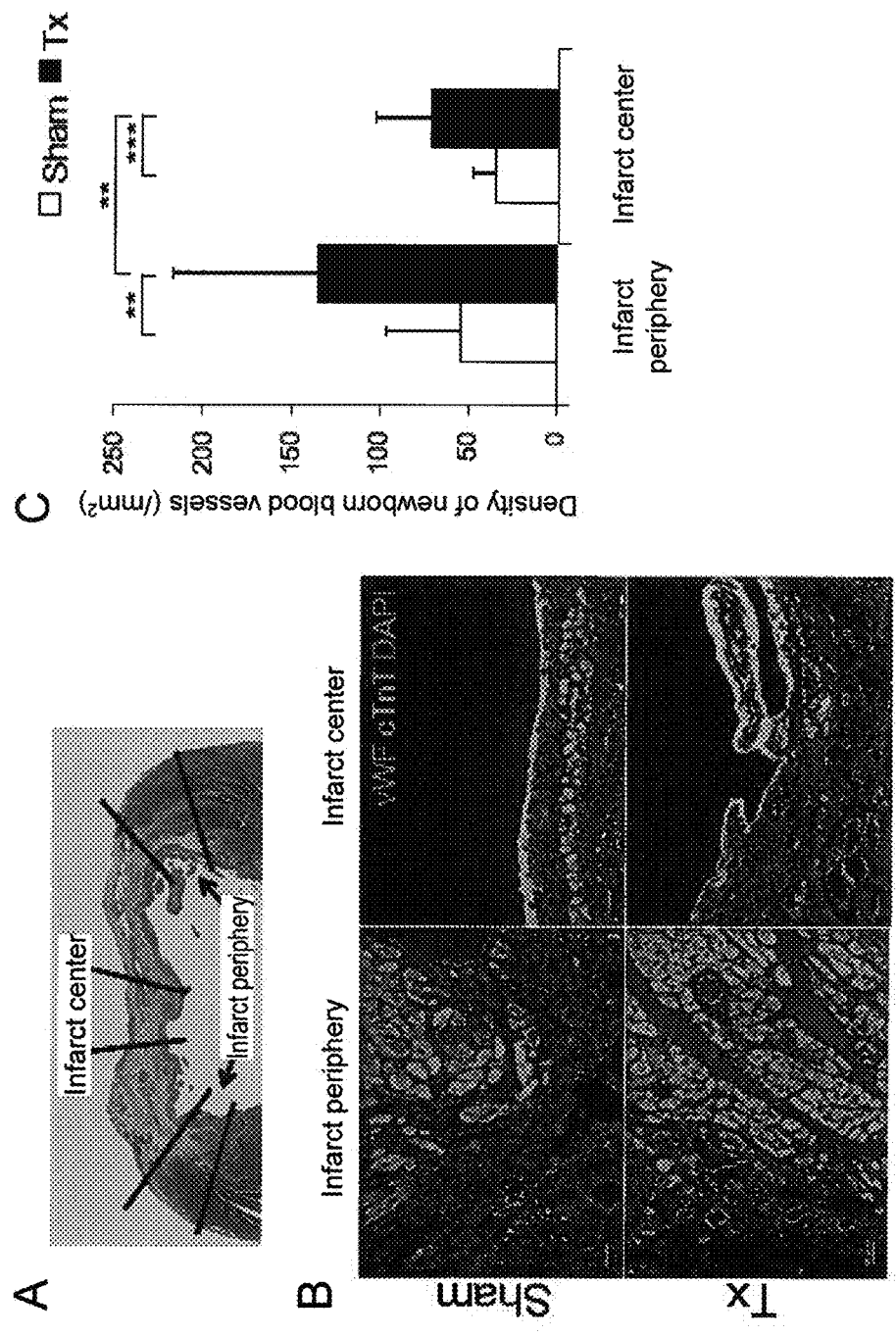

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: primer

<400> SEQUENCE: 1
```

```
ccagcacata ggagagatga gctt                                         24

<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
caaggctcac agtgattttc tgg                                          23

<210> SEQ ID NO 3
<211> LENGTH: 25
<212> TYPE: DNA
<213> ORGANISM: Artificial
<220> FEATURE:
<223> OTHER INFORMATION: primer

<400> SEQUENCE: 3
catccgtaaa gacctctatg ccaac                                        25

<210> SEQ ID NO 4
<211> LENGTH: 19
<212> TYPE: DNA
<213> ORGANISM: Artificial
<220> FEATURE:
<223> OTHER INFORMATION: primer

<400> SEQUENCE: 4
atggagccac cgatccaca                                               19
```

METHOD FOR PRODUCING MYOCARDIAL SHEET FROM EMBRYONIC STEM CELL

CROSS-REFERENCE TO RELATED APPLICATIONS

This application is a national phase of International Application PCT/JP2012/059427, filed Mar. 30, 2012, which was published on Oct. 4, 2012, as WO 2012/133945, which claims the benefit of JP Application No. 2011-076235, filed Mar. 30, 2011. The respective contents of these applications are incorporated herein by reference in their entirety.

TECHNICAL FIELD

The present invention relates to a method for producing a myocardial sheet using cardiomyocytes, endothelial cells, and mural cells, which are derived from embryonic stem cells.

The present invention further relates to a therapeutic agent for heart diseases comprising a myocardial sheet obtained by the above method.

BACKGROUND ART

Adult cardiomyocyte does not almost grow, and thus the lack of cardiomyocytes caused by ischemic heart disease or the like becomes an irreversible damage. At present, there are no clinically used medicines or treatments that exhibit efficacy in substitution of a myocardial scar with a functional contractile tissue. Hence, novel therapies for the regeneration of normal cardiomyocytes are highly desired. A replacement therapy that involves the administration of separately produced cardiomyocytes has been proposed. In connection with such replacement therapy, administration of cardiomyocytes that are sheet-shaped so as to enable successful engraftment of the cells to the heart of a recipient has been examined (Non-patent Literature 1, Patent Literature 2). However, because this therapy is problematic in that the cell amount in such a sheet is insufficient and thus therapeutic effects cannot be obtained as expected, it is suggested that the sheets should be laminated before administration (Non-patent Literature 2).

Meanwhile, methods of using fetal cardiomyocytes, myoblasts, cardiac myoblasts generated from adipose tissue-derived stem cells and embryonic stem cell-derived cardiomyocytes, have been exemplified as supply sources of cardiomyocytes for sheet preparation (Patent Literature 2, Non-patent Literature 3).

However, there has been no report that cardiac functions were improved as a direct effect by administration of sheets formed only from embryonic stem cell-derived cells.

PRIOR ART LITERATURE

Patent Literature

Patent Literature 1: International Patent Publication No. WO2002/008387
Patent Literature 2: JP Patent Publication (Kohyo) No. 2007-528755A

Non-Patent Literature

Non-patent Literature 1 Shimizu, T et al, Biomaterials 24: 2309-2316, 2003

Non-patent Literature 2 Shimizu, T et al. FASEB J. 20: 708-10, 2006
Non-patent Literature 3 Bel, A et al. Circulation. 122: S118-23, 2010

SUMMARY OF THE INVENTION

The present invention relates to a method for producing a myocardial sheet using cardiomyocytes, endothelial cells, and mural cells, which are derived from embryonic stem cells, and to a therapeutic agent for heart diseases comprising the thus obtained myocardial sheet. Therefore, an objective of the present invention is to provide a myocardial sheet produced by mixing cells obtained by inducing embryonic stem cells to differentiate into cardiomyocytes, endothelial cells, and mural cells.

To achieve the above objective, the present inventors have now found that such a sheet can be obtained by producing Flk/KDR-positive cells from embryonic stem cells, mixing a group of cells comprising cardiomyocytes, endothelial cells, and mural cells, which are prepared from the Flk/KDR positive cells on a culture dish coated with a temperature-responsive polymer, and culturing the resulting cell group. The present inventors have further confirmed that the cell group can survive after transplantation of the sheet and thus that cardiac functions can be improved.

Based on the above results, the present inventors have now succeeded in treating a myocardial infarct model using myocardial sheets produced using the cardiomyocytes, endothelial cells, and mural cells, which are derived from embryonic stem cells, thereby having completed the present invention.

Specifically, the present invention encompasses the following characteristics.

[1] A method for producing a sheet from embryonic stem cell-derived cardiomyocytes, endothelial cells, and mural cells, comprising the following steps (a) and (b) of:
    (a) producing Flk/KDR positive cells, cardiomyocytes, endothelial cells, and mural cells separately from embryonic stem cells; and
    (b) forming a sheet by mixing the Flk/KDR positive cells with the cardiomyocytes, endothelial cells, and mural cells.
[2] The method according to [1], wherein the Flk/KDR positive cells are induced by culturing embryonic stem cells on a gelatin-coated culture vessel.
[3] The method according to [1] or [2], wherein in the step (a), the cardiomyocytes are produced by culturing the Flk/KDR positive cells in the presence of cyclosporin A.
[4] The method according to [1] or [2], wherein in the step (a), the endothelial cells and the mural cells are produced by culturing the Flk/KDR positive cells in the presence of VEGF and cAMP.
[5] The method according to any one of [1] to [4], wherein in the step (b), the Flk/KDR positive cells are cultured for 1 to 7 days, preferably 3 days, and then mixed with cardiomyocytes, endothelial cells, and mural cells.
[6] The method according to any one of [1] to [5], wherein in the step (b), the sheet is formed using a culture vessel coated with a temperature-responsive polymer.
[7] The method according to any one of [1] to [6], wherein in the step (b), the sheet is formed by further culturing the mixed cells in the presence of VEGF.
[8] The method according to any one of [1] to [7], further comprising a step of laminating the sheets.
[9] The method according to [8], wherein the laminated sheet consists of three layers.

[10] A therapeutic agent for heart diseases, comprising a myocardial sheet obtained by the method of any one of [1] to [9].

[11] Mixed cells comprising cardiomyocytes, endothelial cells, and mural cells.

[12] The cells according to [11], wherein the content of the cardiomyocytes is at least 40%.

[13] The cells according to any one of [11] and [12], wherein the content of the endothelial cells is at least 3%.

[14] The cells according to any one of [11] to [13], wherein the content of the mural cells is at least 50%.

[15] The cells according to any one of [11] to [14], wherein the mixed cells are sheet-shaped.

[16] The cells according to any one of [11] to [15], wherein the cardiomyocytes, endothelial cells, and mural cells are cells produced from embryonic stem cells.

[17] The cells according to any one of [11] to [16], wherein the mixed cells are human-derived cells.

This description includes all or part of the contents as disclosed in the description and/or drawings of Japanese Patent Application No. 2011-076235, from which the present application claims the priority.

BRIEF DESCRIPTION OF THE DRAWINGS

The application file contains at least one drawing executed in color. Copies of this patent application publication with color drawing(s) will be provided by the Office upon request and payment of the necessary fee.

In FIG. 1, APC denotes Allophycocyanin, PE denotes phycoerythrin, SSC denotes side scatter, GFP denotes green fluorescent protein, and FITC denotes fluorescein isothiocyanate.

FIG. 2A shows: (upper panel) the sirius red staining image showing the layer formation of extracellular matrix confirmed in the adhesion portion of the cell culture dish stained with sirius red; (middle panel) the H-E staining image showing a sheet composed of 3-4 layers of cells stained with H-E; and (lower panel) the cTnT staining image showing the presence of cTnT positive cell as a major constituent of the sheet. FIG. 2B shows the cross-sectional image of the sheet observed with a multiple-photon laser microscope. FIG. 2C shows the surface image of the sheet. Dispersed ECs were confirmed among CMs.

In FIG. 3C, when an electrode with the highest peak negative potential is designated as a zero point (at the lower part of the figure), time differences (seconds) between the peak negative potential at the zero point and the peak negative potentials of electrodes are shown in different colors. Conduction from the lower part to the upper part was observed.

In FIG. 4, SF denotes serum free, TNFa denotes tumor necrosis factor-α, IGF-1 denotes insulin-like growth factor-1. VEGF denotes vascular endothelial cell growth factor, bFGF denotes basic fibroblast growth factor, IFNr denotes interferon-γ, EGF denotes epithelial growth factor, and HGF denotes hepatocyte growth factor.

FIG. 6A shows the result of comparison with a value of the cardiac fibroblast (CF) sheet as measured by quantitative RT-PCR. FIG. 6B shows the results of ELISA using culture supernatants. In FIG. 6(B), ** denotes p<0.01.

FIG. 7A shows typical undifferentiated colonies (arrow) in Group 1 (left panel: immediately after collection of myocardial sheet) and increased colonies in Group 2 (right panel; LIF was added and then cells were continuously cultured for 3 days). FIG. 7B shows the number of undifferentiated colonies in each Group. FIG. 7C shows the average colony area of each Group. FIG. 7D shows the sizes of all colonies of each Group in order. Sizes of at least 5,000 $\mu m^2$ are shown in red. Colonies with sizes of at least 5,000 $\mu m^2$ were determined to be Positive and colonies with sizes of 5,000 $\mu m^2$ or less were determined to be Negative. Then the number of colonies of each Group and the percentage thereof is shown in the table. Fisher's exact probability test was used as a significance difference test.

FIG. 9A shows changes with time in M-mode measurements for groups to which myocardial sheets were transplanted. It was observed that the wall motion of infarct walls (upper portions in the figures) was restored with time after transplantation. FIG. 9B shows left ventricular fractional shortening (FS), FIG. 9C shows left ventricular fractional area change (FAC), and FIG. 9D shows changes with time in increase of systolic thickening (all of them are indicators for left ventricular contractile capacity). In FIG. 9D, the treatment group exhibited a significant increase in the infarct wall (left panel), but no change was observed in the non-infarct wall (right panel). In week 4 (Tx4w) after treatment, the wall thickness in the treatment group was restored to a level almost the same as that of a non-infarct wall. FIG. 9E shows changes with time in akinetic lesion (AL) (an indicator for the range of infarction sites). FIG. 9F shows the rate of change in diastolic left ventricular lumen area relative to that before treatment (PreTx) (an indicator for left ventricular dilatation). In FIG. 9, PreTx denotes before treatment, Tx2w denotes week 2 after treatment. Tx4w denotes week 4 after treatment, and LV denotes left ventricle. Furthermore, † denotes p<0.05, ‡ denotes p<0.01 (vs PreTx, paired t-test), * denotes p<0.05,  denotes p<0.01, and * denotes p<0.001 (vs. sham (B) (C) (D) or Tx (E) (F), unpaired t-test).

FIG. 10A shows pressure-volume curve shifts depending on decrease in preload in the sham group (left panel) and in the treatment group (right panel). The left ventricular elastance of end systole (Ees) is represented by the slope of a straight line indicated by the arrow. FIG. 10B shows the Ees (left panel) and the time constant (Tau) (right panel) for the sham group (white) and the same for the treatment group (black). Ees denotes left ventricular contractile capacity (a high Ees level indicates high contractile capacity), Tau denotes left ventricular dilation capacity (a low Taw level indicates high dilation capacity). In FIG. 10, *** denotes p<0.001, and N.S. denotes no significant difference.

FIG. 11A shows the results of FISH (mouse-derived cells: yellow) and cTnT immunostaining image (red) on day 1 (left), in week 1 (middle), and in week 4 (right) after transplantation. A site where cells survived on day 28 (Tx-d28) after transplantation is indicated with an arrow. FIG. 11B is an immunostaining image showing connexin43 (green) on day 7 after transplantation. The lower left area enclosed by a white line shows an image of normal myocardium. The structure shown in FIG. 11B was not so organized as in normal myocardium, but connexin43-positive sites (arrows) were observed within myocardial masses that had survived.

In FIG. 12, scale bar=25 μm.

FIG. 13A shows sirius red staining images of the sham group (left) and the treatment group (Tx: right). In the treatment group, wall thinning was suppressed and a decrease in infarct region was observed. FIG. 13B shows the percentage of the infarct region in the sham group (white) and the percentage of the same in the treatment group (Tx: black) (left) and wall thickness (right).

FIG. 14A shows the results of FISH (mouse-derived cells: yellow), cTnT immunostaining images (red), and von Willebrand factor (vWF) immunostaining images (green) on day 1 (Tx-d1: left), on day 3 (Tx-d3: middle), and on day 7 (Tx-d7: right) after transplantation. FIG. 14B shows each magnified image of a fluorescence microscope on day 3 after transplantation. vWF-positive sites with luminal structures were partially observed within GFP-positive graft-derived cardiomyocyte mass. Furthermore, when observed in bright field, erythrocytes were observed within the lumen. FIG. 14C shows the results of FISH on day 3 after transplantation and each magnified fluorescence microscopic "vWF immunostaining" image. Mouse signals (yellow) were observed in some of newborn blood vessels.

FIG. 15 shows the results of measuring a newborn blood vessel density (a capillary density) in week 4 after transplantation. FIG. 15A shows a Masson trichrome staining image of the treatment group in week 4 after transplantation, specifically in infarct center (Central-MI) and infarct periphery (Peri-MI). FIG. 15B shows stained images (cTnT (red) and vWF (green)) in the infarct periphery and the infarct center of the treatment group (Tx) and the same of the sham group. Within both the periphery and the center, vWF-positive sites with luminal structures were found to be significantly formed in the treatment group. FIG. 15C shows capillary densities in the Central-MI site and the same in the Peri-MI site of each group shown in FIG. 15A. In FIG. 15C,  denotes p<0.01, and * denotes p<0.001 (unpaired t-test).

MODES FOR CARRYING OUT THE INVENTION

Figure 1:
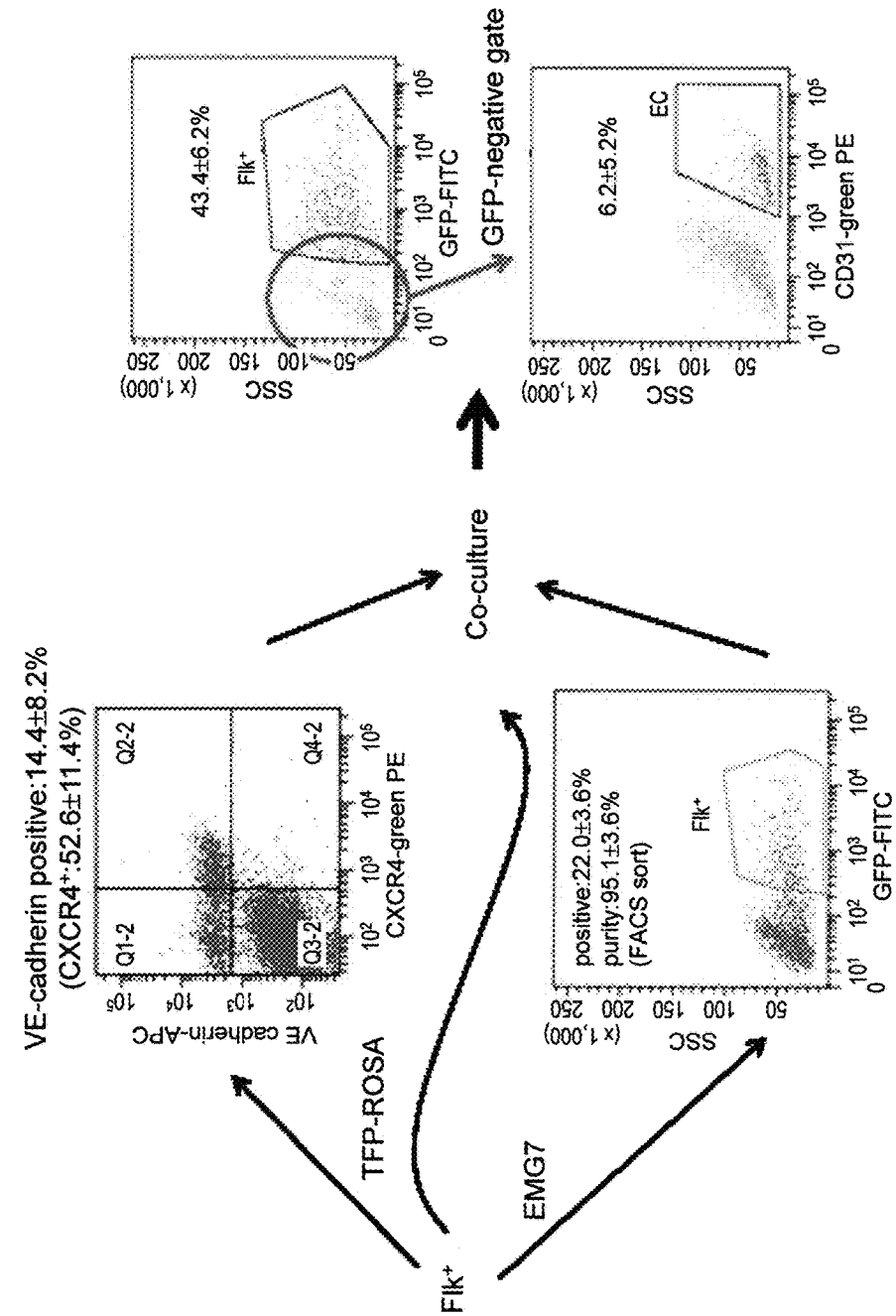
FIG. 1 shows the FACS results of CMs (cardiomyocytes) and EC components before they were co-cultured in temperature-sensitive dishes and after formation of sheets.

The present invention will be described below in detail.

The present invention relates to: a method for producing a myocardial sheet from embryonic stem cells, comprising the steps of (a) producing Flk/KDR positive cells, cardiomyocytes, endothelial cells, and mural cells separately from embryonic stem cells, and (b) mixing the Flk/KDR positive cells with the cardiomyocytes, endothelial cells, and mural cells, so as to form a myocardial sheet; and to a therapeutic agent comprising the myocardial sheet obtained by this method, the agent being used for heart diseases such as ischemic heart disease, as described above.

<Embryonic Stem Cell>

ES cells are stem cells having pluripotency and proliferation potency based on self-replication, which are established from inner cell masses of early embryos (e.g., blastocysts) of mammals such as humans and mice.

ES cells are embryo-derived stem cells from the inner cell masses of the blastocysts that are embryos after the morula stage at the 8-cell stage of fertilized egg. ES cells have namely, pluripotency, which is the ability to differentiate into any cells composing an adult body, and proliferation potency based on self-replication. ES cells were discovered in mice in 1981 (M. J. Evans and M. H. Kaufman (1981), Nature 292: 154-156) and then ES cell lines were established for primates such as humans and monkeys (J. A. Thomson et al. (1998), Science 282: 1145-1147; J. A. Thomson et al. (1995), Proc. Natl. Acad. Sci. U.S.A., 92: 7844-7848; J. A. Thomson et al. (1996), Biol. Reprod., 55: 254-259; J. A. Thomson and V. S. Marshall (1998), Curr. Top. Dev. Biol., 38: 133-165).

ES cells can be established by removing inner cell masses from blastocysts of fertilized eggs of a target animal and culturing the inner cell masses on fibroblasts as feeder cells. Also, cell maintenance by subculture can be performed using a culture medium supplemented with substances such as leukemia inhibitory factor (LIF) and basic fibroblast growth factor (bFGF). Methods for establishment and maintenance of human or monkey ES cells are described in U.S. Pat. No. 5,843,780; Thomson J A, et al. (1995), Proc Natl. Acad. Sci. U.S.A. 92: 7844-7848; Thomson J A, et al. (1998), Science. 282: 1145-1147; H. Suemori et al. (2006), Biochem. Biophys. Res. Commun., 345: 926-932; M. Ueno et al. (2006), Proc. Natl. Acad. Sci. U.S.A. 103: 9554-9559; H. Suemori et al. (2001), Dev. Dyn., 222: 273-279; H. Kawasaki et al. (2002), Proc. Natl. Acad. Sci. U.S.A. 99: 1580-1585; and Klimanskaya I, et al. (2006), Nature. 444: 481-485.

As the culture medium for preparation of ES cells, a DMEM/F-12 culture medium supplemented with 0.1 mM 2-mercaptoethanol, 0.1 mM nonessential amino acids, 2 mM L-glutamate, 20% KSR and 4 ng/ml β-FGF can be used, for example. Human ES cells can be maintained using the same culture medium under wet atmosphere (2% $CO_2$/98% air) at 37° C. (O. Fumitaka et al. (2008), Nat. Biotechnol., 26: 215-224). Also, ES cells require subcultures or passages every 3 to 4 days. At this time, the subculture or passage can be performed using 0.25% trypsin and 0.1 mg/ml collagenase IV in PBS containing 1 mM $CaCl_2$ and 20% KSR, for example.

ES cells can be generally selected by the Real-Time PCR method using the expression of gene markers (e.g., alkaline phosphatase, Oct-3/4, and Nanog) as indicators. In particular, human ES cells can be selected using the expression of a gene marker (e.g., OCT-3/4, NANOG, and ECAD) as indicators (E. Kroon et al. (2008), Nat. Biotechnol., 26: 443-452).

Human ES cell lines, such as WA01 (H1) and WA09 (H9) are available at the WiCell Research Institute, and human ES cell lines such as KhES-1, KhES-2, and KhES-3 are available at the Institute for Frontier Medical Sciences, Kyoto University (Kyoto, Japan).

<Differentiation Medium>

Examples of differentiation media usable for production of Flk/KDR positive cells (also referred to as "Flk$^+$ cells"), cardiomyocytes, endothelial cells, and mural cells (for production of a myocardial sheet) are as described below.

Medium used for culturing animal cells can be prepared as a basal medium. Examples of such basal medium include IMDM medium, medium 199, Eagle's Minimum Essential Medium (EMEM), αMEM medium, Doulbecco's modified Eagle's Medium (DMEM), Ham's F12 medium, RPMI 1640 medium, Fischer's medium, and mixtures thereof. Medium may contain serum or may be serum free.

Medium may further contain, if necessary, one or more serum substitutes, such as albumin, transferrin, Knockout Serum Replacement (KSR) (serum substitute for FBS upon ES cell culture), fatty acids, insulin, collagen precursor, trace elements, 2-mercaptoethanol, and 3'-thiol glycerol, as well as one or more substances such as lipids, amino acids, nonessential amino acids, vitamins, growth factors, cytokines, antibiotics, antioxidants, pyruvate, buffering agent, and inorganic salts.

<Method for Producing Flk/KDR Positive Cells from Embryonic Stem Cells>

In the present invention, the term "Flk/KDR positive cells" refers to cells expressing at least Flk/KDR. Here, the term "Flk/KDR" refers to Flk1 or KDR, which is a receptor of vascular endothelial growth factor (VEGF). An example of Flk1 is NCBI accession No. NM_010612. An example of KDR is NCBI accession No. NM_002253.

Flk/KDR positive cells can be prepared by inducing differentiation of embryonic stem cells by an arbitrary method (Yamashita J, et al, Nature. 408, 6808, 2000 or Yamashita J K, et al, FASEB J. 19:1534-6, 2005). For example, under conditions where undifferentiation cannot be maintained (LIF is not added to a medium or feeder cells are not used), Flk/KDR positive cells can be prepared by culturing for 4-5 days using a culture dish coated with a substance such as collagen, gelatin, poly-L-lysine, poly-D-lysine, laminin, fibronectin, Matrigel™ (Becton, Dickinson and Company).

<Method for Producing Cardiomyocytes from Embryonic Stem Cells>

In the present invention, the term "cardiomyocytes" refers to cells expressing at least cardiac troponin T (cTnT) or αMHC. An example of cTnT in the case of humans is NCBI accession No. NM_000364, and an example of the same in the case of mice is NM_001130174. An example of αMHC in the case of humans is NCBI accession No. NM_002471, and an example of the same in the case of mice is NM_001164171.

Embryonic stem cells are caused to form cell masses (embryoid bodies) by suspension culture, and thus the differentiation thereof into cardiomyocytes can be induced. In addition to this example, a known method can be employed as a method for inducing the differentiation of embryonic stem cells into cardiomyocytes. Examples of such a method are not particularly specified. For example, differentiation of embryonic stem cells into cardiomyocytes can be induced by a method that comprises inducing differentiation in the presence of a substance suppressing BMP signal transduction (WO2005/033298), a method that comprises adding Activin A and BMP in order, so as to induce differentiation (WO2007/002136), a method that comprises inducing differentiation in the presence of a substance accelerating the activation of the canonical Wnt signaling pathway (WO2007/126077), a method that comprises isolating Flk/KDR positive cells from embryonic stem cells, and then inducing differentiation in the presence of cyclosporin A (WO2009/118928), or the like. In the present invention, a preferable method comprises culturing embryonic stem cells by adhesion culture on a culture vessel, so as to produce Flk/KDR positive cells, and then inducing differentiation in the presence of cyclosporin A. The content of cyclosporin A in medium ranges from 0.1 µg/mL to 30 µg/mL, and preferably ranges from 1 µg/mL to 3 µg/mL, for example, and can be any level as long as it enables the induction of differentiation into cardiomyocytes. The surface of the culture vessel can be coated with a cell supporting substance in order to improve adhesiveness with cells, such as collagen, gelatin, poly-L-lysine, poly-D-lysine, laminin, fibronectin, and Matrigel™ (Becton, Dickinson and Company). The days for culture are not particularly limited and range from 1 to 10 days and are preferably 4 days after culturing Flk/KDR positive cells in the presence of cyclosporin A.

In the present invention, cardiomyocytes may be isolated or purified in advance, or mixed in advance with other cell species. Preferably, cardiomyocytes are isolated and purified cells. As a method for isolation and purification, which is not particularly limited, a method of selecting a cardiomyocyte marker such as N-cadherin as an indicator (Honda M, et al, Biochem Biophys Res Commun. 29, 351, 877-82, 2006), a method of selecting mitochondria within cardiomyocytes as an indicator (WO2006/022377), or a method of selecting cells capable of surviving under low nutrition conditions (WO2007/088874) can be employed, for example.

<Method for Producing Endothelial Cells and Mural Cells from Embryonic Stem Cells>

In the present invention, the term "endothelial cells" refers to cells expressing at least any one of PE-CAM, VE-cadherin, and von Willebrand factor (vWF). Also, the term "mural cells" refers to cells expressing at least Smooth muscle actin (SMA). Here, an example of PE-CAM in the case of humans is NCBI accession No. NM_000442, and an example of the same in the case of mice is NM_001032378. An example of VE-cadherin in the case of humans is NCBI accession No. NM_001795, and the same in the case of mice is NM_009868. An example of vWF in the case of humans is NCBI accession No. NM_000552, and the same in the case of mice is NM_011708. An example of SMA in the case of humans is NCBI accession No. NM_001141945 and the same in the case of mice is NM_007392.

Embryonic stem cells are caused to form cell masses (embryoid bodies) by suspension culture, and thus can be induced to differentiate into endothelial cells or mural cells. In addition to this method, a known method can be employed as a method for inducing differentiation of embryonic stem cells into endothelial cells or mural cells, and is not particularly specified. For example, the differentiation of embryonic stem cells into cardiomyocytes can be induced using a method comprising isolating Flk/KDR positive cells from embryonic stem cells, and then inducing differentiation in the presence of VEGF and cAMP (Yamashita J, et al. Nature. 408: 92-6, 2000). The contents of VEGF and cAMP in a medium are not limited as long as differentiation to endothelial cells or mural cells can be induced. The content of VEGF ranges from 25 ng/mL to 150 ng/mL, and preferably ranges from 50 ng/mL to 100 ng/mL, for example. Examples of the term "cAMP" to be used herein include its derivatives thereof (e.g., 8-bromo-cAMP). The content of cAMP ranges from 0.1 mmol/L to 2 mmol/l, and preferably ranges from 0.5 mmol/L to 1 mmol/L, but the examples thereof are not limited thereto. The days for culture are not particularly limited, and range from 1 to 10 days and are preferably 3 days after culturing Flk/KDR positive cells in the presence of VEGF and cAMP.

In the present invention, endothelial cells or mural cells may be isolated and purified from each other, or endothelial cells or mural cells may be present together with other cell species.

<Mixed Cells Comprising Cardiomyocytes, Endothelial Cells, and Mural Cells>

In the present invention, mixed cells containing simultaneously cardiomyocytes, endothelial cells, and mural cells that are obtained using the above method can be produced.

At this time, the content of cardiomyocytes is, for example, 10%, 20% or more, 30% or more, 40% or more, or 50% or more, 90% or less, 80% or less, 70% or less, 60% or less or 50% or less. The preferable content thereof is 40% or more and is more preferably 40% or more and 50% or less.

Similarly, the content of endothelial cells is, for example, 1%, 2% or more, 3% or more, 4% or more, 5% or more or 10% or more, 50% or less, 40% or less, 30% or less, 20% or less, or 10% or less. The preferable content thereof is 3% or more, and is more preferably 3% or more and 10% or less.

Similarly, the content of mural cells is, for example, 10%, 20% or more, 30% or more, 40% or more, 50% or more, or 60% or more, 90% or less, 80% or less, 70% or less, or 60% or less. The preferable content thereof is 20% or more, 30% or more, 40% or more or 50% or more, and is more preferably 50% or more and 60% or less.

In the present invention, the above mixed cells may be isolated as a cell culture, and are preferably sheet-shaped mixed cells.

<Method for Producing Myocardial Sheet>

A myocardial sheet comprises various cells that form the heart or blood vessels, and is a sheet-shaped cell aggregate wherein cells are connected to each other via intercellular junction. Here, examples of various cells that form the heart or blood vessels include the above cardiomyocytes, endothelial cells, and mural cells.

In the present invention, preferably the myocardial sheet has electrical coupling and orientation among cells, and secretes VEGF out of cells.

The myocardial sheet is produced by mixing cells comprising at least cardiomyocytes, endothelial cells and mural cells prepared by the above method and then culturing the mixed cells. The number of each type of cells to be cultured at this time ranges from $1 \times 10^4$ to $1 \times 10^6$, for example. In the present invention, cells other than cardiomyocytes, endothelial cells, and mural cells may also be contained. Preferably, a myocardial sheet is produced by culturing the above embryonic stem cell-derived Flk/KDR positive cells for 1 to 7 days, preferably 3 days, and then mixing and culturing the cells with cardiomyocytes, endothelial cells, and mural cells. Here, for the purpose of preventing tumor formation after transplantation of the myocardial sheet, it is desired to mix cells except for undifferentiated cells retaining multipotency. Undifferentiated multipotent cells can be recognized by Nanog or Oct3/4, for example.

After mixing each type of these cells, VEGF may be added to the culture medium and then the cells may be further cultured. The days for culture at this time may range from 1 to 10 days and are preferably 4 days.

For the above culture, a culture vessel coated with a temperature-responsive polymer that is prepared by polymerization with a (meth)acrylamide compound, a N- (or N,N-di) alkyl-substituted (meth)acrylamide derivative (JP Patent Publication (Kokai) No. 2010-255001 A), or a vinyl ether derivative may also be used. Preferably the culture vessel to which poly-N-isopropylacrylamide has been fixed is used. Such culture vessel can be purchased as UpCell from CellSeed Inc.

In the present invention, the size of a myocardial sheet depends on a culture vessel, and preferably has an area sufficient for covering a site to be subjected to transplantation.

The thus prepared myocardial sheets may be used after lamination, and are preferably 3 layers of myocardial sheets. Lamination can be performed as follows. Myocardial sheets are laminated in a culture medium (preferably, myocardial sheets are laminated so that they are slightly shifted from each other), the culture medium is removed, and thus the sheets can be adhered to each other. When a plural number of myocardial sheets are laminated, this can be performed simultaneously, or preferably the procedure is performed for each layer.

The myocardial sheet(s) produced by the above method has the following characteristics, for example.

The myocardial sheet(s) comprises at least cardiomyocytes, endothelial cells, and mural cells, wherein the percentages of cells composing the myocardial sheet(s) are, but are not limited to the following examples: cardiomyocytes 35-50%, endothelial cells 0.5-7%, and mural cells 45-63%.

Endothelial cells are scattered among cardiomyocytes.

VEGF is expressed and secreted.

<Treatment of Heart Disease>

The myocardial sheet that is provided by the present invention can be used as a therapeutic agent for heart diseases of animals (preferably, humans). A method for treating a heart disease is achieved by placing the myocardial sheet(s) so as to cover a desired portion. Here, the procedure of "placing . . . so as to cover a desired portion" can be performed using a technique known in the art. Upon placement, when a desired portion is large, the myocardial sheet(s) can be placed surrounding the tissue. Also, the myocardial sheet(s) can be placed several times to the same portion in order to obtain desired effects. When placement is performed several times, placement is desirably performed at sufficient time intervals so that the myocardial sheet(s) can successfully survive in the tissue to perform angiogenesis.

Examples of heart diseases in the present invention include diseases such as heart failure, ischemic heart disease, myocardial infarct, cardiomyopathy, myocarditis, hypertrophic cardiomyopathy, dilated-phase hypertrophic cardiomyopathy, and dilated cardiomyopathy, or lack of myocardial tissues caused by damages.

EXAMPLES

The present invention will be described more specifically by the following examples, but the scope of the present invention is not limited by these specific examples.

Example 1

Preparation of Myocardial Sheet

A mouse ES cell line (EMG7) that had been prepared so as to control EGFP expression using an αMHC promoter as described in Yamashita J K, et al. FASEB J. 19: 1534-6, 2005 was used.

Flk+ cells were prepared by a previously reported method (Yamashita J, et al. Nature. 408: 92-6, 2000 or Yamashita J K, et al. FASEB J. 19: 1534-6, 2005). In brief, Flk positive cells were prepared by culturing EMG7 or 20D17 on a gelatin-coated dish for 4 days using a differentiation medium (αMEM supplemented with 10% fetal calf serum and $5 \times 10^5$ mol/L 2-mercaptoethanol), and then purifying Flk positive cells by FACS.

Mixed endothelial and mural cells were prepared from the Flk+ cells obtained by the above method using a previously reported method (Yamashita J, et al. Nature. 408: 92-6, 2000 or Yurugi-Kobayashi T, et al. Arterioscler Thromb Vasc Biol. 26: 1977-84, 2006). In brief, mixed cells were obtained by culturing cells on a gelatin-coated dish for 3 days using the differentiation medium supplemented with 50 ng/ml VEGF and 0.5 mmol/L 8-bromo-cAMP.

Cardiomyocytes were prepared from the Flk+ cells obtained with the above method using a previously reported method (WO2009/118928 or Yan P, et al. Biochem Biophys Res Commun. 379: 115-20, 2009). In brief, cardiomyocytes were obtained by culturing cells on OP9 cells treated with mitomycin C for 4 days using differentiation medium supplemented with 1-3 μg/mL Cyclosporin-A, and then separating a GFP positive fraction.

Myocardial sheets were prepared by the following method using the above plurality of types of cells. $2.5 \times 10^4$ to $4.0 \times 10^4$ Flk+ cells were seeded on a temperature-sensitive culture dish (UpCell, CellSeed Inc.) and then cultured using the differentiation medium. On day 3 after the initiation of culture, the above $5.0 \times 10^5$ mixed cells of endothelial cells and mural cells and the above $5.0 \times 10^5$ cardiomyocytes were seeded in the same culture dish, and then cultured using the differentiation medium supplemented with VEGF at 37° C. The resultant cells were returned to room temperature on day 4 after addition of cardiomyocytes (day 7 after the initiation of culture), so that the cells were detached in the form of a sheet from the culture dish. Thus a myocardial sheet was obtained. In addition, medium exchange was performed on day 2 after mixing 2 types of cells.

Example 2

Cellular Composition of Myocardial Sheet

The myocardial sheet prepared as described above from EMG7 was isolated using 0.25% trypsin, and then labeled with a PE (phycoerythrin) conjugated anti-CD31 antibody. The percentages of cardiomyocytes (CMs), endothelial cells (ECs), and mural cells (MCs) were determined based on the positive rates of GFP (FITC) and PE in the cells using FACS. The results are shown in FIG. 1. The percentages were calculated to be: CM: 43.4±6.2%, EC: 3.3±2.6%, and MC: 53.3±8.2%.

Example 3

Histological Evaluation of Myocardial Sheet

Figure 2:
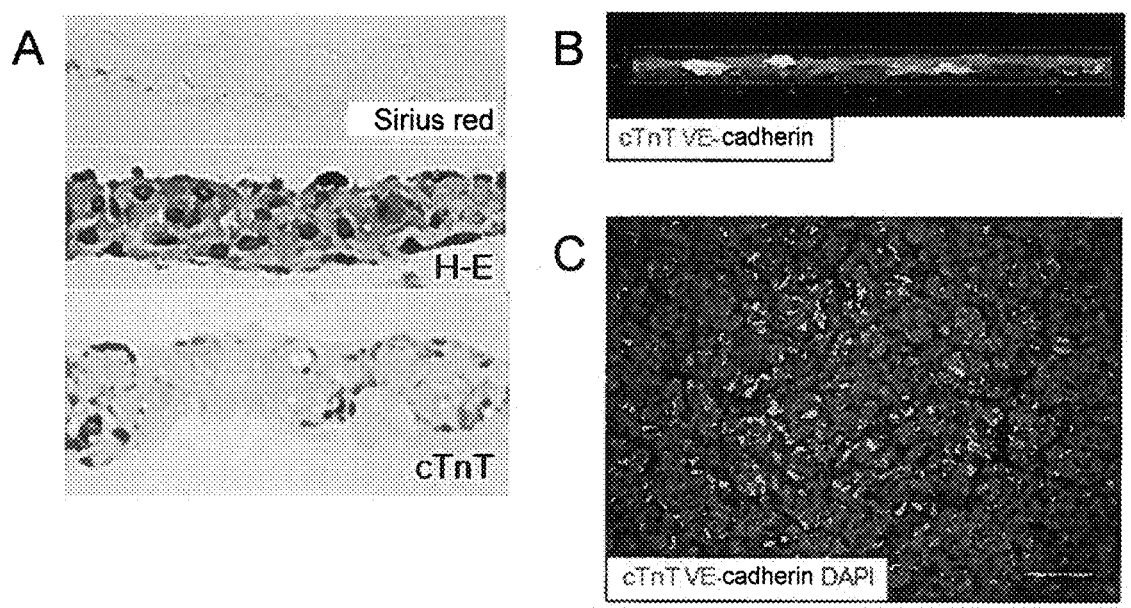
In FIG. 2, H-E denotes hematoxylin•eosin, cTnT denotes cardiac troponin T, and scale bar=200 µm.

To perform histological evaluation, the myocardial sheet prepared from EMG7 was fixed using 4% PFA (paraformaldehyde). After blocking with 1% skimmed milk, CM and EC were labeled using antibodies (primary antibody: mouse anti-cTnT, rat anti-VE-Cadherin, secondary antibodies: anti-mouse Alexa Flour 546, anti-rat Alexa Flour 488). After nuclear staining using DAPI (4',6-diamino-2-phenylindole), the sheet was observed with a multiple-photon laser microscope (LSM 510, Carl-Zeiss) or a fluorescence microscope (BZ-9000, Keyence) (FIG. 2B and FIG. 2C). Furthermore, the resultant cells were fixed with 4% PFA, subjected to dehydration, delipidization, dealcoholization, and then paraffin penetration, and then embedded. 6 μm sections were subjected to hematoxylin•eosin staining, sirius red staining, or immunostaining (HRP/DAB emission) for cTnT, in a manner similar to the above (FIG. 2A). As a result, it was demonstrated that the thus collected sheets retained the extracellular matrix (FIG. 2A upper, sirius red staining). It was also demonstrated that the sheet consisted of 3-4 layers of cells. Moreover, it was observed that ECs were scattered among CMs; the CM being a major constituent of the cell sheet.

Example 4

Electrophysiological Evaluation of Myocardial Sheet

Figure 3:
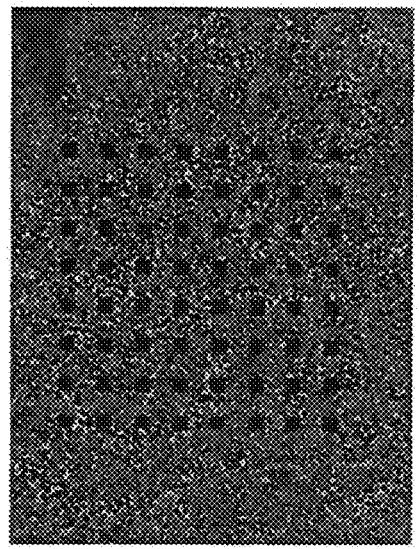
FIG. 3A is the image of a sheet adhered onto MED64 probe.
FIG. 3B shows the extracellular electric potential of each electrode.
FIG. 3C shows the distribution of potentials measured in FIG. 3B.
Figure 3:
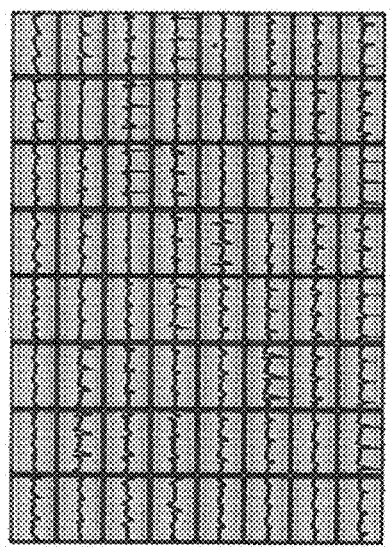
Figure 3:
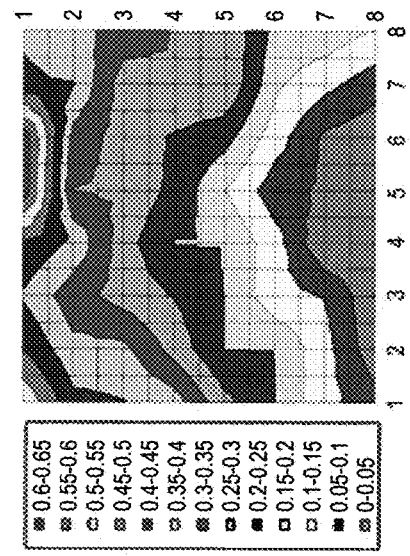

For electrophysiological evaluation, the myocardial sheet prepared from EMG7 was left to stand on an electrode in a culture dish (culture dish with an electrode, MED64 system, Alpha MED Scientific Inc.) coated with 0.1% gelatin. Subsequently, the medium was aspirated and the sheet was then incubated at 37° C. for 30 minutes, so as to fix the electrode and the sheet. The electrical potential of each electrode was then measured to record the conduction of electric potential on the sheet was recorded. The results are shown in FIG. 3. Through the measurement of extracellular electrical potentials, it was confirmed that the heart beat was continuously electrically conducted unidirectionally (FIG. 3C).

Example 5

Cytokine Production Capacity of Myocardial Sheet

Figure 4:
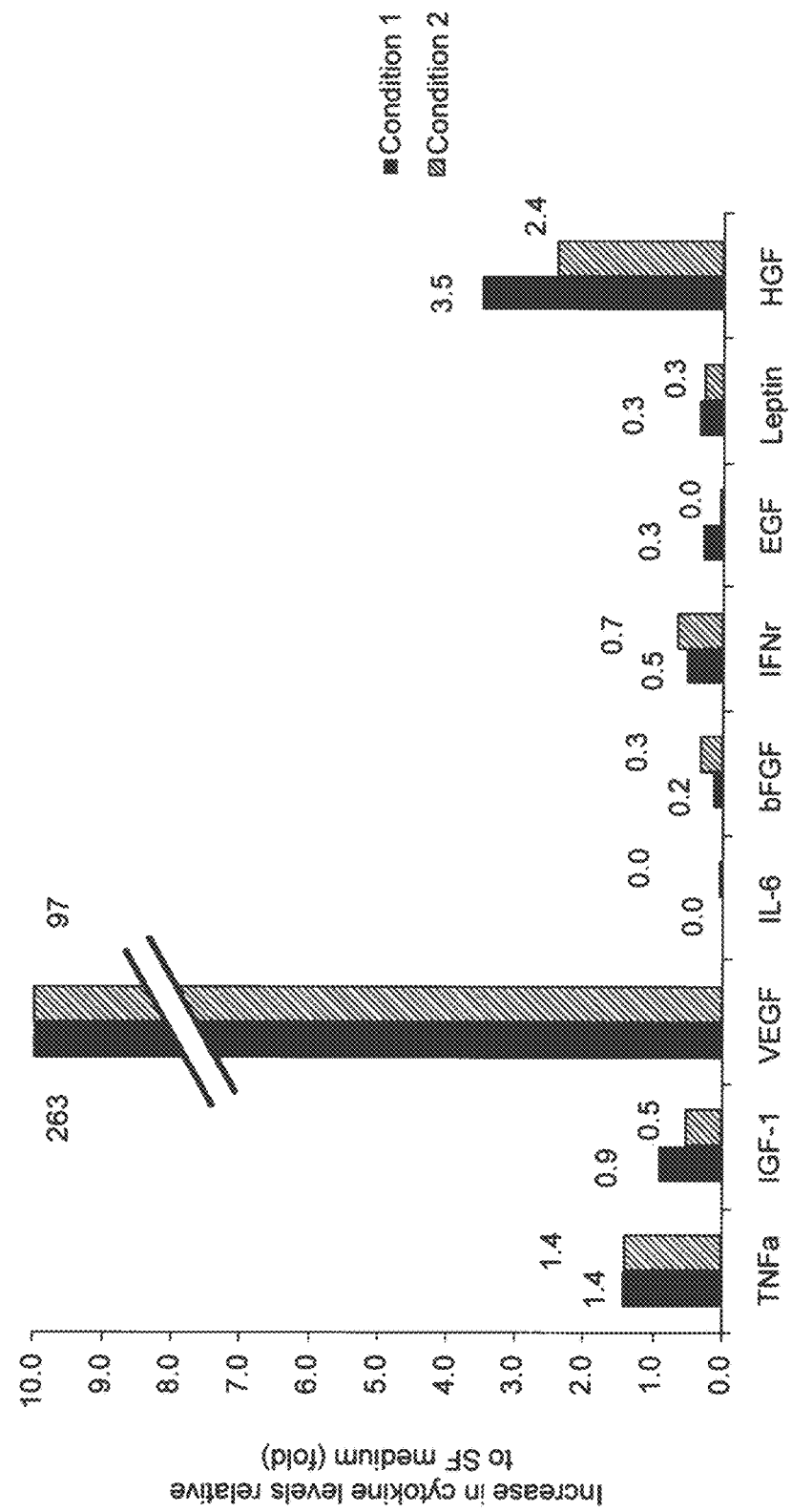
FIG. 4 shows the results of measuring each cytokine level in culture supernatants by ELISA. During (Condition 1) and after (Condition 2) sheet formation, the amounts of VEGF were found to be extremely higher than serum-free media.

The levels of cytokines (TNFα, IGF-1, VEGF, IL-6, bFGF, IFNγ, EGF, Leptin, and HGF) in culture supernatants during (Condition 1) and after (Condition 2) formation of myocardial sheets prepared from EMG7 were measured by ELISA (enzyme-linked immunosorbent assay) (HGF: mouse HGF EIA kit, IIM, all other cytokines: mouse angiogenesis ELISA strip, Signosis). The results are shown in FIG. 4. It was demonstrated that in both cases (during and after the formation of the myocardial sheets), VEGF was produced at very high levels, among cytokines involved in angiogenesis (TNFα, IGF-1, VEGF, IL-6, bFGF, IFNγ, EGF, Leptin, and HGF).

Condition 1: Two days after the addition of cardiomyocytes, the cells were washed twice with a serum-free medium (αMEM supplemented with $5 \times 10^5$ mol/L 2-mercaptoethanol). Two days after culturing with serum-free medium, the culture supernatant was collected and used for measurement of cytokine levels.

Figure 5:
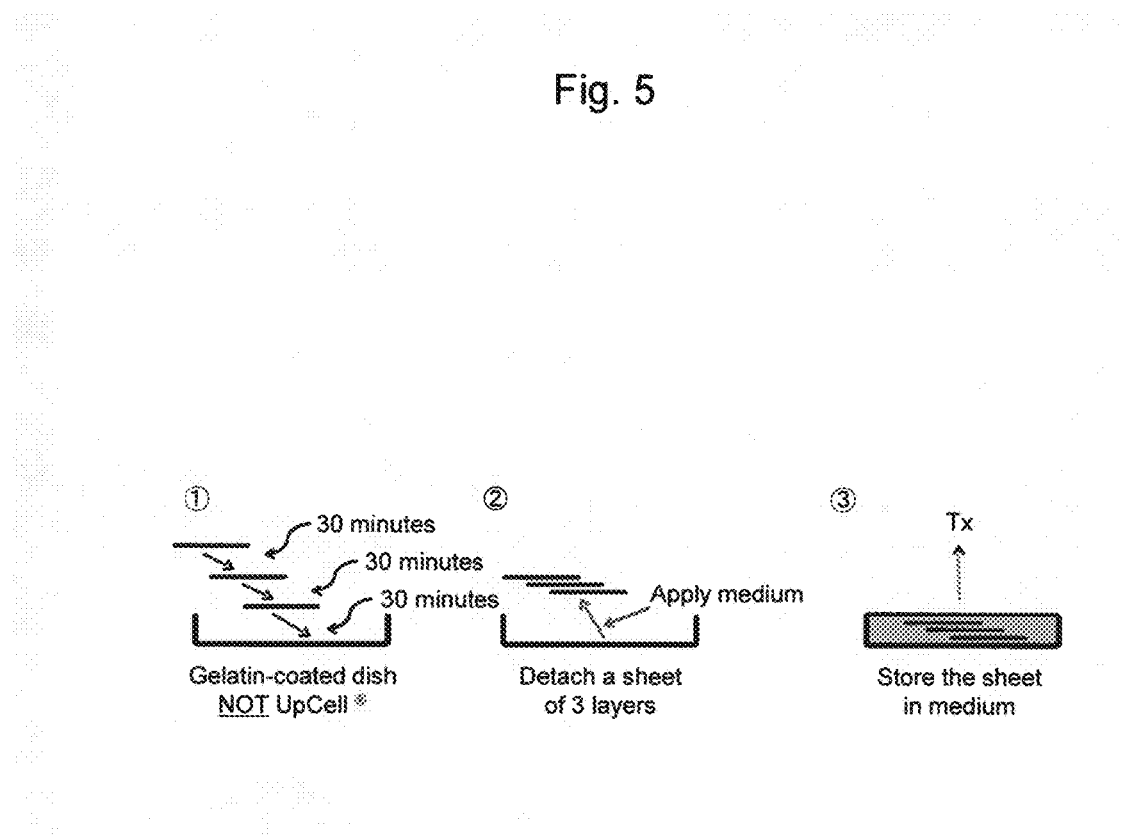
FIG. 5 is a schematic diagram showing a method for lamination of cell sheets.

Condition 2: A myocardial sheet prepared by the above method was spread and left to stand on a gelatin-coated dish, and then the medium was aspirated. After fixing the culture dish and the sheet, medium was added, and the cells were then incubated at 37° C. for 30 minutes. Another myocardial sheet was spread and left to stand on the sheet fixed to the dish. The medium was aspirated for lamination. This procedure was repeated for the lamination of three layers. The $2^{nd}$ and the $3^{rd}$ layers were laminated so that each layer was shifted slightly from the original sheet. Subsequently, medium was applied using Pipetman along the bottom of the culture dish, and thus the laminated cell sheet was detached from the culture dish (FIG. 5). The laminated myocardial sheet was washed twice with serum-free medium, and then continuously cultured with serum-free medium. After 3 hours, the culture supernatant was collected and used for the measurement of cytokine levels.

Example 6

VEGF Production Capacity of Myocardial Sheet

Figure 6:
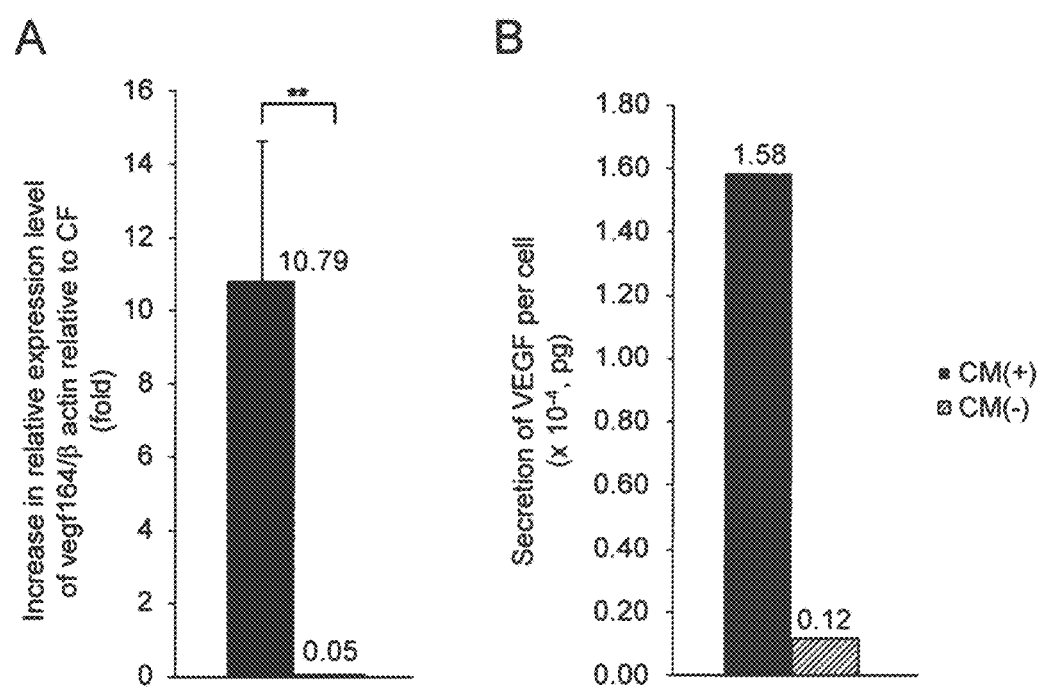
FIG. 6 shows graphs showing the results of comparing sheets prepared by adding cardiomyocytes (CMs) with sheets prepared by adding no CM for VEGF production.

RNA was extracted from the above prepared myocardial sheets using RNeasy mini (QIAGEN) and the expression level of vegfl64 was then measured by quantitative RT-PCR (Step One Plus, Applied Biosystems, forward primer of vegfl64: 5'-CCAGCACATAGGAGAGATGAGCTT-3' (SEQ ID NO: 1) and reverse primer of vegfl64: 5'-CAAGGCTCACAGTGATTTTCTGG-3' (SEQ ID NO: 2), forward primer of b-actin: 5'-CATCCGTAAAGACCTC-TATGCCAAC-3' (SEQ ID NO: 3) and reverse primer of b-actin: 5'-ATGGAGCCACCGATCCACA-3' (SEQ ID NO: 4)). At this time, as a control, cell sheets prepared using neonatal mouse-derived cardiac fibroblasts (CF) were also used. The results are shown in FIG. 6A. It was demonstrated that myocardial sheets prepared from EMG7 expressed vegfl64 at levels much higher than that of the CF sheets. Furthermore, during the preparation of the above myocardial sheets, culture supernatants were aspirated before collection (before the temperature was lowered to room temperature) of the CM (+) and CM (−) sheets (where CM (+) represents sheets to which cardiomyocytes had been added and CM (−) represents sheets to which no cardiomyocyte had been added). After washing twice with serum-free medium, the sheets were cultured with serum-free medium for 3 hours, the supernatants were collected to measure VEGF levels (Quantikine mouse VEGF, R&D). The results are shown in FIG. 6B. It was demonstrated that the CM (+) sheet secreted VEGF at a much higher level than that of the CM (−) sheet.

Example 7

Evaluation of Contamination of Undifferentiated Cells into Myocardial Sheets

Figure 7:
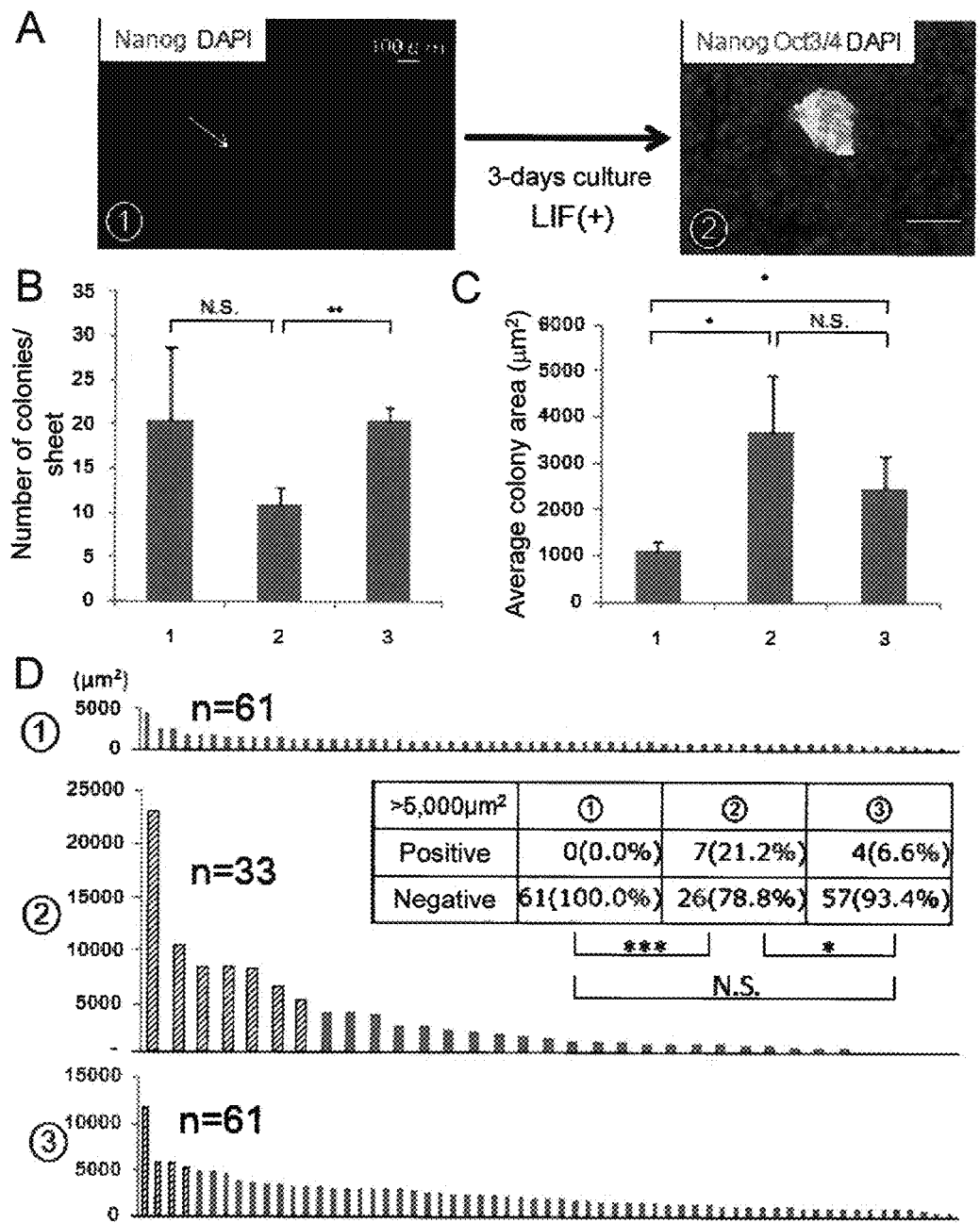
In FIG. 7, Scale bar=100 µm, * denotes p<0.05, *** denotes p<0.001, and N.S. denotes no significant difference.

Myocardial sheets were collected, and then left to stand on gelatin-coated dishes. Medium was aspirated and then the sheets were incubated at 37° C. for 30 minutes, thereby fixing the dishes and the sheets. The sheets were divided into 3 groups, with three sheets per group. After fixation with 4% PFA, blocking was performed with % skimmed milk. Nanog or Oct3/4 positive cells were labeled using antibodies (primary: mouse anti-Oct 3/4 and rabbit anti-Nanog, secondary: anti-mouse Alexa Flour 488 and anti-rat Alexa Flour 546), and the results were measured using a fluorescence microscope. The results are shown in FIG. 7. It was confirmed that small colonies of undifferentiated cells were contaminated within the sheet (Group1) immediately after collection. It was also confirmed that while the size of the undifferentiated colonies increased in the sheet of Group 2 (which was continuously cultured under the LIF (+) environment), but the increase of the same was suppressed in LIF (−) (Group3).

Group 1: Fluorescent immunostaining was performed immediately after collection of a myocardial sheet.

Group 2: After collection of a myocardial sheet, the sheet was continuously cultured in ES cell medium, supplemented with LIF (leukemia inhibiting factor) (Yamashita J, et al. Nature. 408: 92-6, 2000) for 3 days, followed by fluorescent immunostaining.

Group 3: After 3 days of continuous culture in LIF-free ES cell medium, fluorescent immunostaining was performed.

Example 8

Transplantation of Myocardial Sheet into Disease Rat Model

A subacute myocardial infarct (MI) model was produced by the following method using athymic immunodeficient rats (10-13 weeks of age, and 250 g to 330 g) (F344/N Jcl-rnu/rnu) (Clea Japan Inc.). Respiratory support was provided using a ventilator for rats. The rats were anesthetized by isoflurane inhalation, Subsequently, under artificial respiration with a small amount of oxygen, the heart was exposed by pericardiotomy (left intercostal thoracotomy). The anterior descending coronary artery was ligated with a 6-0 polypropylene suture at the periphery of the first major septal branch. After confirmation of decreased contraction and color tone changes in the peripheral perfusion area (when no such changes were confirmed, ligation was performed again), the incision was closed using a 4-0 polypropylene suture. After 6 days, the presence or absence of MI was confirmed by heart ultrasonography (Vivid7, GE Yokogawa Medical). Models with left ventricular fractional shortening (FS) of more than 40% were excluded as inappropriate models.

Figure 8:
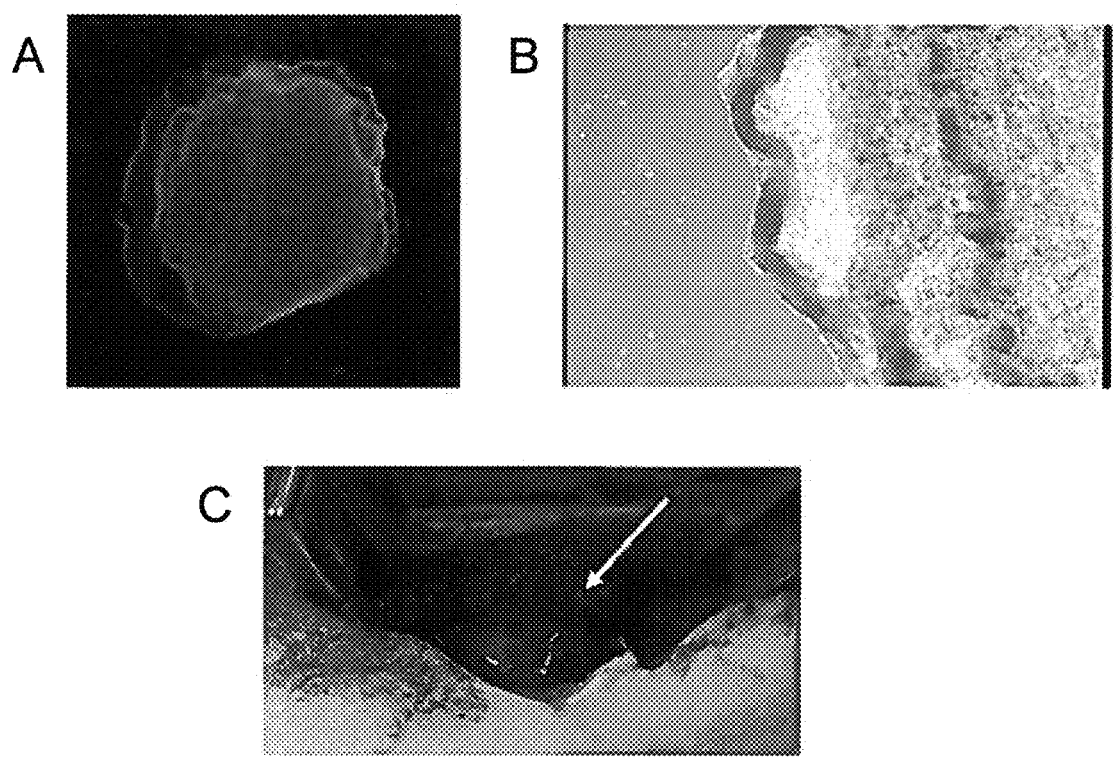
FIG. 8A shows the gross appearance of the sheets after lamination.
FIG. 8B shows an optical microscopic image of the sheets after lamination.
FIG. 8C shows the gross appearance after transplantation of sheets. The arrow indicates laminated sheets.

Myocardial sheets prepared from EMG7 (FIG. 8) were transplanted on day 7 after introduction of MI. Three myocardial sheets were laminated to use for transplantation (FIG. 5) by the above method. The transplantation was performed as follows. Anesthesia was induced in the rat MI model with diethyl ether, respiratory support was provided using a ventilator for rats, and then anesthesia was maintained with isoflurane. After left intercostal thoracotomy, adhesions between the lungs and thoracic walls were carefully detached, so as to expose the myocardial infarct site. The laminated myocardial sheets were then transplanted onto the myocardial infarct site. The site was left to stand for 15 minutes, and then closed with a 4-0 polypropylene suture. For the sham surgery group, myocardial infarct sites were exposed and then closed after 15 minutes, following the same procedure.

All 12 cases that had been observed until week 4 after transplantation survived. No teratoma formation was observed for 9 cases, for which the hearts had been visually observed. No teratoma was observed by heart ultrasonography for the remaining 3 cases.

Example 9

Evaluation of Cardiac Functions Resulting from Transplantation of Myocardial Sheet Heart ultrasonography was performed in weeks 2 and 4 after transplantation. In week 4 after transplantation, cardiac functions were measured by left ventricular pressure-volume curve measurement (cardiac catheterization test:

MIKRO-TIP catheter system, Millar instruments). The treatment group and the sham group were each evaluated and the results were compared.

Figure 9:
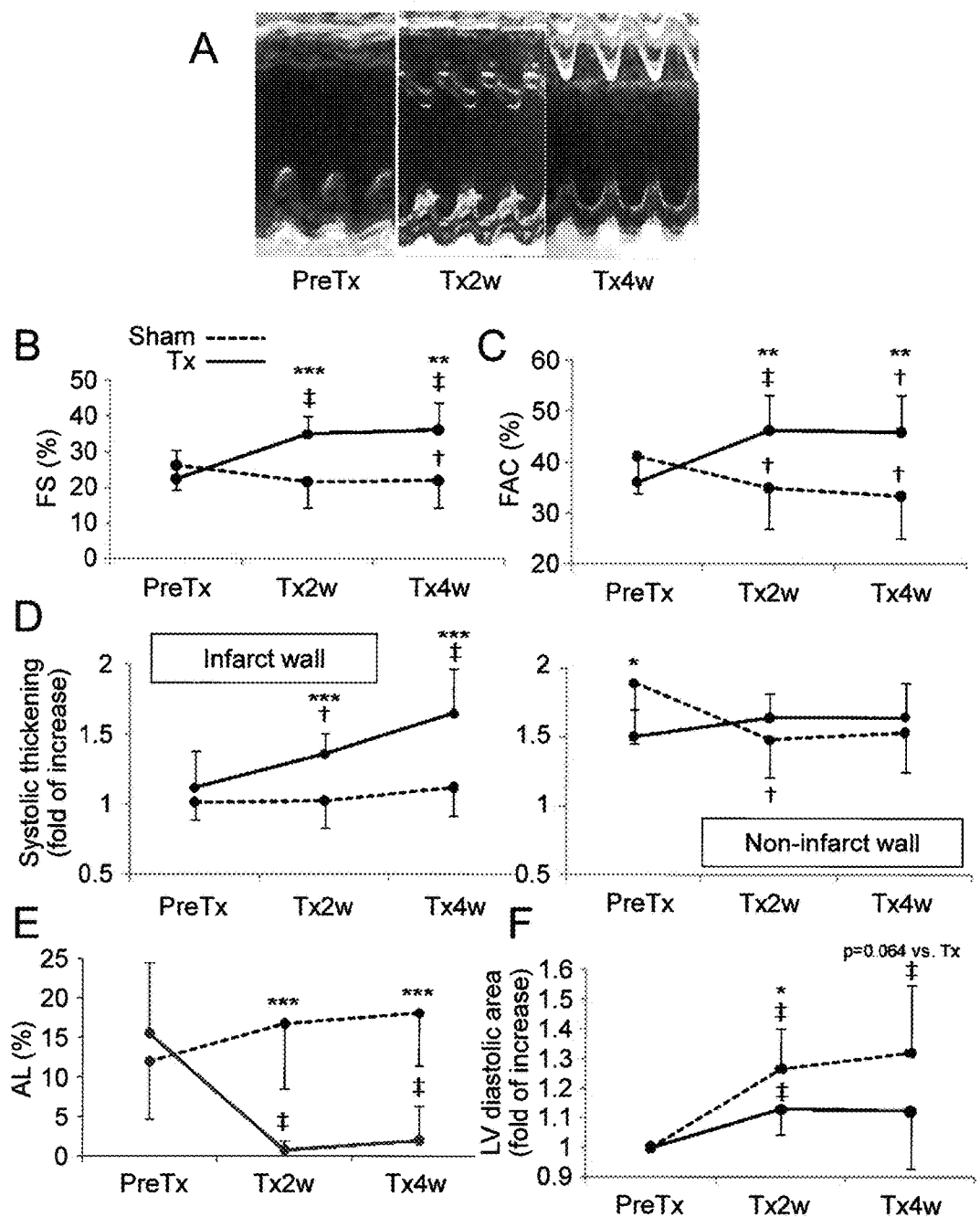
FIG. 9 shows the results of heart ultrasonography.

Heart ultrasonography was performed by the following method (each group; n=9). After anesthesia induction with diethyl ether, respiratory support was provided using a ventilator for rats. Anesthesia was maintained with isoflurane, so as to achieve anesthetic depths (R-R intervals of 120-200 msec). Subsequently, measurement was performed using a 10S probe (4.0-11.0 MHz). In M-mode, diastolic and systolic septum diameter, left ventricular luminal diameter, and the posterior wall diameter were measured, and then left ventricular fractional shortening (FS) and systolic thickening were calculated. In B-mode, diastolic and systolic left ventricular luminal area and left ventricular circumference were measured, and then left ventricular fractional area change (FAC) and akinetic lesion (AL) were calculated. During these measurements, artificial respiration was stopped, so as to eliminate bias caused by respiration: As a result, FS, FAC, and systolic thickening indicating left ventricular contractile capacity were found to be improved in the treatment group in both weeks 2 and 4 after treatment, compared with those before treatment. In addition, these values were significantly higher than those in the sham group. The infarct range represented by AL decreased in week 2 and week 4 after treatment compared with the same before treatment, and was more significantly limited in the treatment group than the sham group. Regarding diastolic left ventricular luminal area (the rate of changes from the area before treatment), diastolic left ventricular dilatation was significantly greater in the sham group in, week 2 compared to the treatment group (FIG. 9F).

Figure 10:
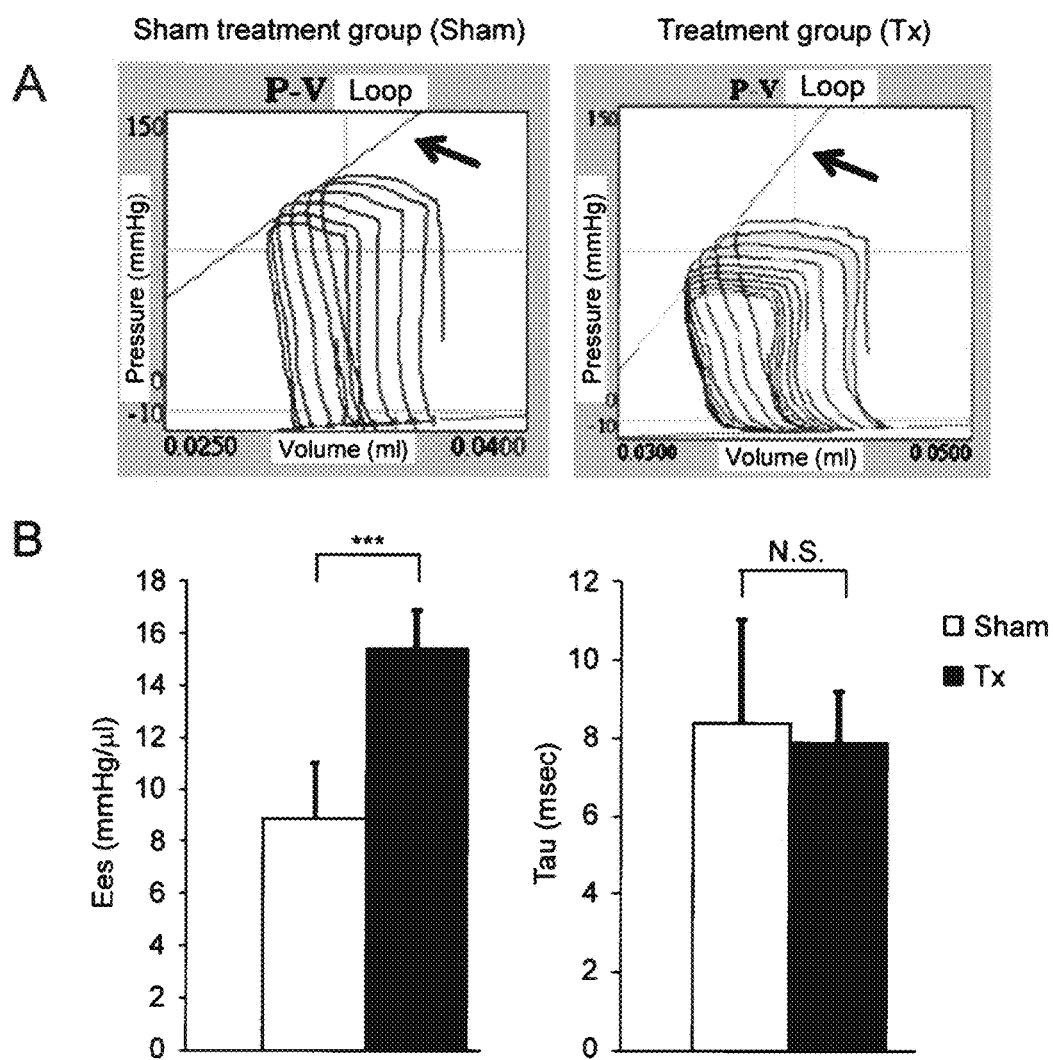
FIG. 10 shows the results of measuring left ventricular pressure-volume curve.

The measurement of left ventricular pressure-volume (PV) curves (i.e., cardiac catheterization test) was performed using the following method (each group; n=8). After anesthesia induction with diethyl ether, respiratory support was provided using a ventilator for rats, and then anesthesia was maintained with isoflurane. A conductance catheter (2Fr) was inserted into the right internal carotid artery, and then introduced into the left ventricle. The left ventricular pressure-volume curve was measured, and the time constant (Tau) was calculated. Laparotomy was performed below the diaphragm with the catheter inserted therein, inferior vena cava compression was performed, and thus the elastance of end systole (Ees) was calculated from the shift of pressure-volume curves caused by decreased preload. Artificial respiration was stopped during the measurement, so as to eliminate bias caused by respiration. As a result, the elastance of end systole (Ees), which indicates a left ventricular contractile capacity, was confirmed to be higher in the treatment group. Thus, the results similar to those obtained by heart ultrasonography were obtained. On the other hand, the time constant (Tau) indicating dilation capacity, was found to tend to be somewhat better in the treatment group, but was not statistically significant (FIG. 10).

Example 10

Histological Evaluation of the Myocardial Sheet after Transplantation

Grafted cell survival over time, localization of surviving cells, and morphological changes (maturation) of graft-derived cardiomyocytes were evaluated by the following methods on days 1 and 3, and in weeks 1 and 4 after transplantation. After anesthesia induction with diethyl ether, respiratory support was provided using a ventilator for rats, and then anesthesia was maintained with isoflurane. Midline thoracotomy was performed, and the superior vena cava, left superior vena cava and inferior vena cava were ensured and blocked. A 23G needle was inserted into the apex of the heart to inject a physiological saline solution in order to cause the outflow of blood within the left ventricle, and to simultaneously release the right atrium, so that hyperdiastole and edema of the heart were prevented. After confirmation of the outflow of only the physiological saline solution from the right atrium, 4% PFA was injected in a similar fashion for 45 minutes, so as to fix the tissue (perfusion fixation method). Subsequently, the heart was excised, infiltrated with 4% PFA, and then left to stand overnight at 4° C. The heart was infiltrated with a 15% sucrose solution (4° C., exchanged twice, 24 hours in total), then embedded and frozen using a solution prepared by adding dry ice to isopentane and OCT compound. In addition, a 6 μm section at the center of an infarct site was prepared. After blocking was performed with a blocking agent (Protein Block Serum-Free, DAKO), GFP positive cardiomyocytes were labeled with antibodies (primary antibodies: mouse anti-cTnT, rabbit anti-GFP, and secondary antibody: anti-mouse Alexa Flour 546 or anti-rat Alexa Flour 488), and then observed using a fluorescence microscope (BZ-9000, Keyence).

In addition, a model in week 1 after transplantation was labeled with connexin 43 (primary antibody: rabbit anti-connexin 43, secondary antibody: anti-rabbit Alexa Flour 488) and the presence or absence of the expression of gap junctions at a graft site was observed using a fluorescence microscope (BZ-9000, Keyence).

Subsequently, simultaneously with immunostaining for cTnT, mouse cells in rat heart tissue were detected by the following method using FISH (fluorescence in situ hybridization) probes recognizing species-specific repeat sequences. As the above probes, a rat genomic DNA FISH probe (Cy5 label) and a mouse genomic DNA FISH probe (digoxigenin label) (Chromosome Science Labo Inc.) were used. Tissue sections were pretreated by the following method and then used. After washing tissue sections with PBS, each tissue section was fixed with 4% PFA/PBS for 15 minutes, washed with PBS, and then dehydrated and dried through the use of a series of alcohols. The section was immersed in 10 mM Tris-EDTA (pH 9.0) solution, heated in a microwave oven for 10 minutes, treated with 0.02% pepsin/0.1 N HCN for 10 seconds to 1 minute, washed with PBS, and then dehydrated and dried through the use of a series of alcohols. After application of the rat and the mouse genomic DNA FISH probes to the thus pretreated specimen sections, the sections and probes were simultaneously denatured on a hot plate (80° C.) for 10 minutes, followed by hybridization at 37° C. The thus hybridized chromosome specimens were subjected to a stringency wash at 37° C. with 50% formamide/2×SSC. Signals from rat and mouse nuclei were detected with the use of anti-Dig-Cy3 and the mouse genomic DNA FISH probe signal, respectively. A solution prepared by diluting (1:200) mouse anti-cTnT with Can Get Signal Solution 1 (TOYOBO) to a given concentration was then added dropwise to each section that had been subjected to FISH, followed by a 1 hour of reaction at 37° C. After reaction, the sections were washed with PBST for 5 minutes×3 times. Secondary antibodies (anti-rabbit-Alexa488 and anti-mouse-Alexa 594) diluted 1:500 with Can Get Signal Solution2 were added to be subjected to 30-minutes reaction, thereby performing immunostaining. After reaction, the sections were then washed with PBST for 5 minutes×3 times. Nuclear staining was also performed with DAPI. After staining, genomic DNA probe signals and fluorescence-labeled antibodies were microscopically observed using a Leica CW-4000 system.

Figure 11:
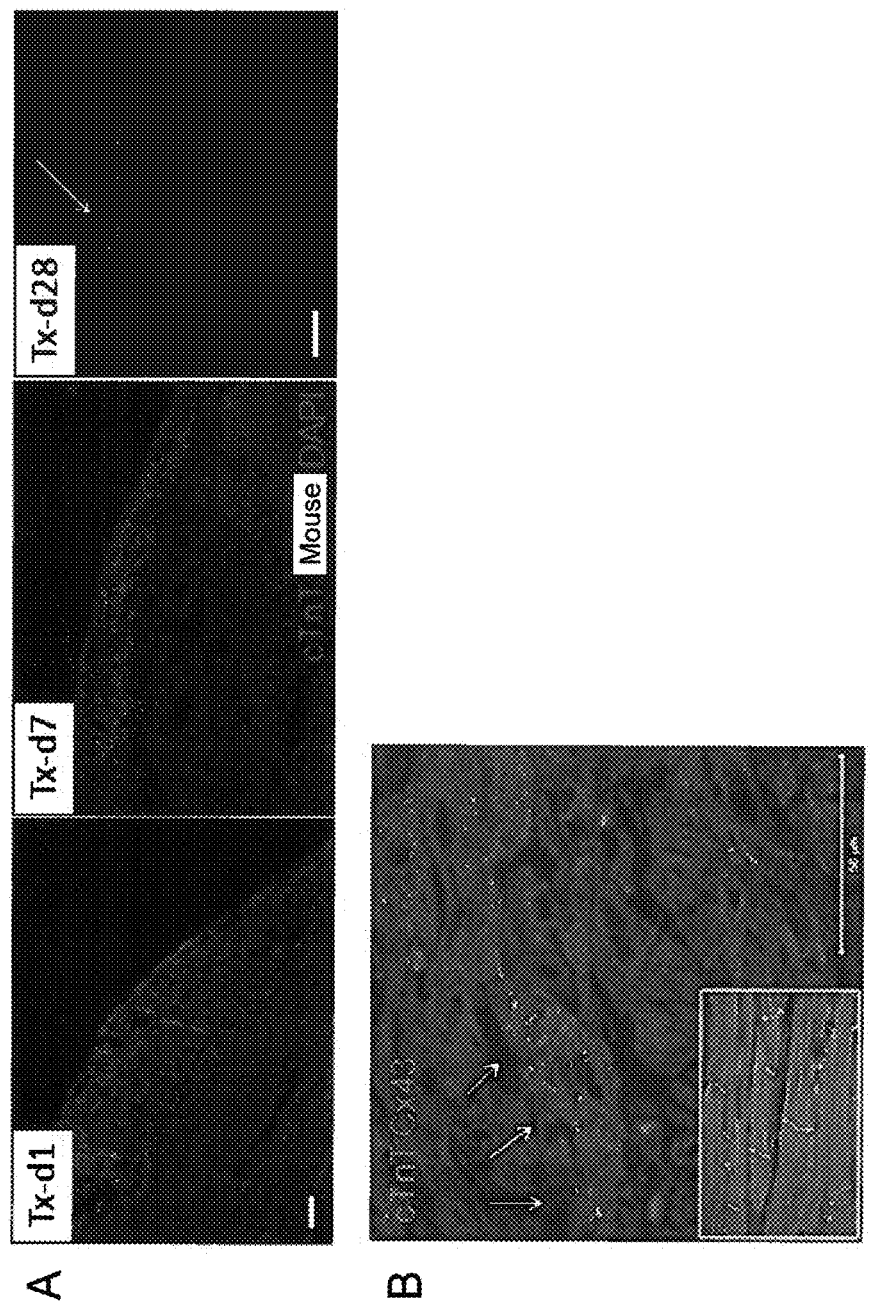
In FIG. 11, Cx43 denotes connexin 43, scale bar=200 μm (A), and scale bar=50 μm (B).
Figure 12:
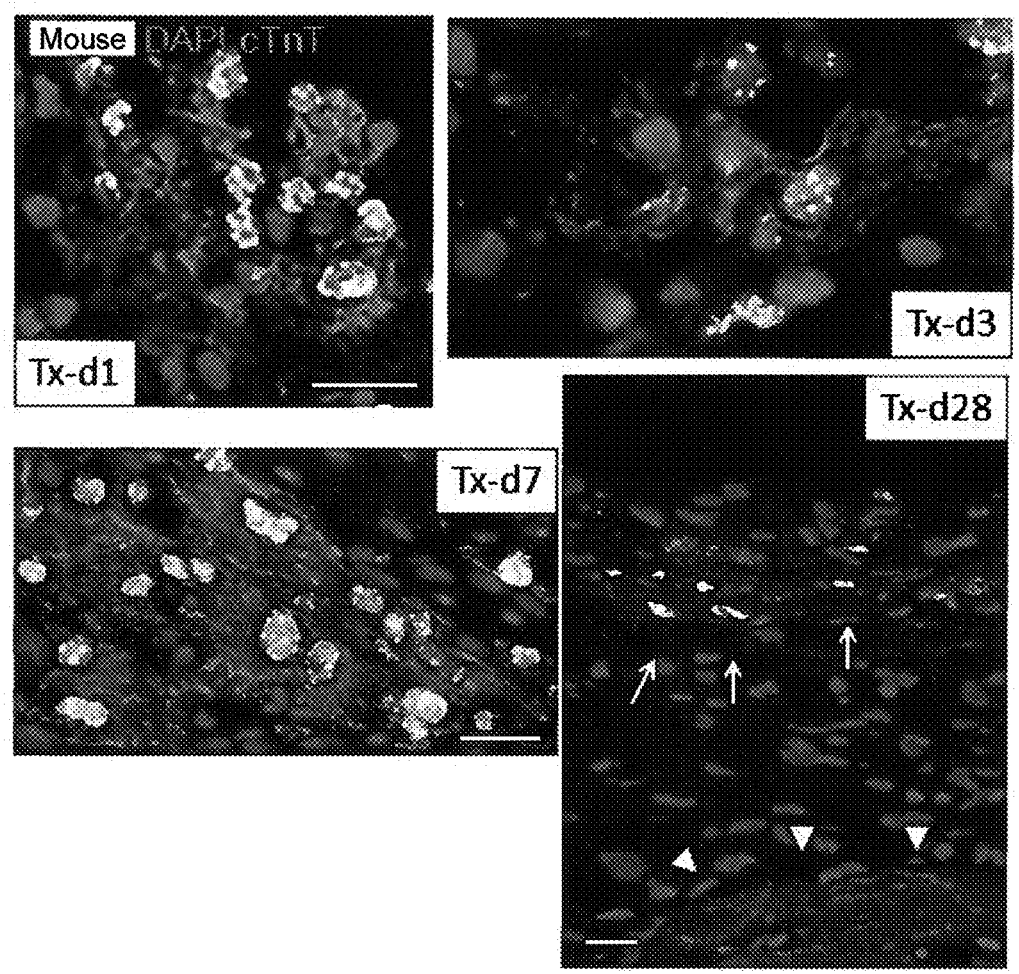
FIG. 12 shows the results of FISH (mouse-derived cells: yellow) for graft-derived (successfully surviving) cardiomyocytes and cTnT immunostaining images (red) of the same on day 1 (Tx-d1), on day 3 (Tx-d3), in week 1 (Tx-d7), and in week 4 (Tx-d28) after transplantation. On day 1 after transplantation, granular cTnT-positive sites were scattered within cytoplasm. However, on day 3 and in week 1 after transplantation, the formation of fibrous structures was observed over time. In week 4 after transplantation, graft-derived cardiomyocytes (arrow) and recipient cardiomyocytes (arrow head) were observed to be almost morphologically the same.

As a result, the number of mouse-derived successfully engrafted (surviving) cells decreased with time. On day 28, a small amount of cells were observed. After day 7, the sites with surviving cells were mainly infarct peripheries, where recipient myocardium remained to a higher extent. Sites where cardiomyocytes had survived were confirmed to gradually form gap junctions on day 7 after transplantation (FIG. 11). Moreover, the cardiac troponin T (cTnT) structure composing cardiomyocyte sarcomeres (supramolecular assembly) became morphologically mature with time after transplantation, as demonstrated by immunostaining for cTnT. In week 4, the cardiac troponin T (cTnT) structure was confirmed to be almost morphologically identical to recipient cardiomyocytes (FIG. 12).

Example 11

Figure 13:
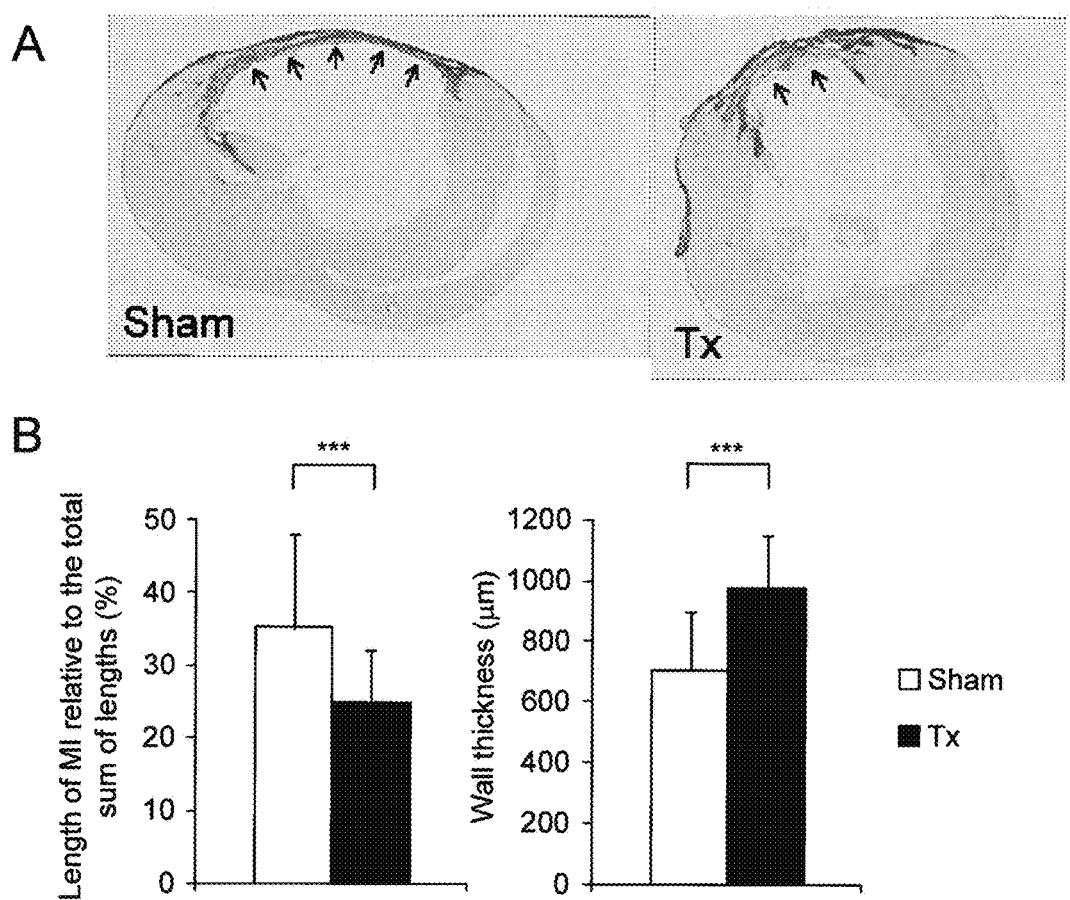
In FIG. 13, *** denotes p<0.001.

Evaluation of Postinfarction Left Ventricular Remodeling by Transplantation of Myocardial Sheets In week 4 after transplantation, five 6-μm thick sections (located at intervals of 50 μm from the infarct center) were prepared per rat, stained with sinus red, and observed with a fluorescence microscope. The length of ventricular lumen and the length of each infarct site were measured, so as to calculate the percentage of the infarct site. Also, the area of each infarct site was divided by its length, so as to calculate the average wall thickness of the infarct site. The calculations were performed separately for the treatment group and the sham group (5 animals each), and then the results were compared. As a result, the infarct regions in the treatment group were more limited than those of the sham group, demonstrating that the wall thinning of an infarct site was suppressed to a higher degree in the treatment group than in the sham group (FIG. 13). It is suggested that these results were due to suppressed postinfarction left ventricular remodeling in the treatment group.

Example 12

Figure 14:
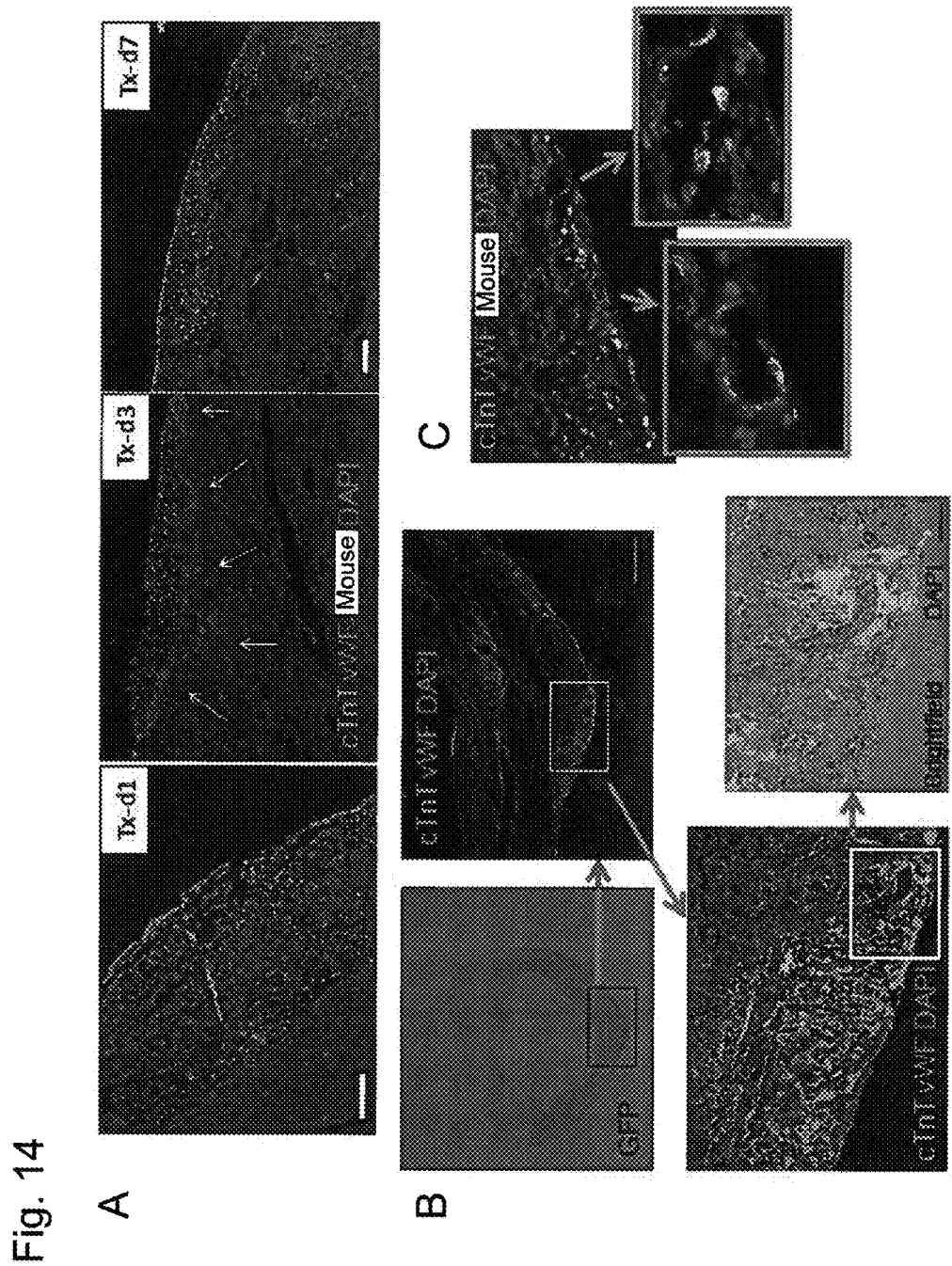
In FIG. 14, Scale bar=200 μM (A), Scale bar=500 μM (B) (upper right), and Scale bar=500 μm (B) (lower right).

Evaluation of Angiogenesis at Graft Sites Due to Transplantation of Myocardial Sheets On day 1, day 3, in week 1, and week 4 after transplantation, immunostaining (1:500) for vWF and FISH were simultaneously performed using sections prepared by a method similar to that of the above method. The number of newborn blood vessels (capillary density) in week 4 in the center (Central-MI) and periphery (Peri-MI) of each infarct site were measured for the treatment group and the sham group. Then the results were compared (randomly selected 5 visual fields per 3 animals). At this time, Masson trichrome staining was performed for one case in the treatment group in order to show the center and the periphery in a figure. For the treatment group, the distribution of newborn blood vessels (e.g., the presence or absence of angiogenesis at sites where graft-derived cardiomyocytes had survived) was observed on day 1, day 3, and in week 1. On day 1 after transplantation, vWF positive cells were scattered within graft sites. On day 3, collections of vWF positive cells surrounding cardiomyocyte masses at the graft sites from inside were observed. However, they did not clearly form any luminal structure and no mouse signals were detected, so these were considered to be collections from the recipient (rat) side. On day 7 after transplantation, the collections observed on day 3 were no longer observed. When the conditions on day 3 after transplantation were further observed with even higher magnification, vWF positive luminal structures were partially observed in graft cell (cardiomyocyte) masses, and erythrocytes were observed within the structures. This demonstrates the growth of newborn blood vessels with blood stream within grafts. Moreover, FISH and vWF immunostaining were simultaneously performed at the same site, demonstrating incorporation of mouse-derived cells into part of newborn blood vessels. It was considered that not only recipient cells, but also graft-derived cells contribute to formation of newborn blood vessels (FIG. 14). In week 4 after transplantation, as described above, the number of graft-derived cells that had survived decreased significantly, however, significantly accelerated angiogenesis in the treatment group was demonstrated by measurement of capillary density. It was also demonstrated that more angiogenesis in the treatment group had taken place in the infarct periphery than in the center (FIG. 15).

INDUSTRIAL APPLICABILITY

Through transplantation of the myocardial sheet of the present invention to a patient's heart disease affected part, normal cardiomyocytes grow and survive, and angiogenesis with blood stream can also be accelerated. Accordingly, the myocardial sheet of the present invention can be used for regenerative medicine for treating heart diseases such as heart failure, ischemic heart disease, myocardial infarct, cardiomyopathy, myocarditis, hypertrophic cardiomyopathy, dilated-phase hypertrophic cardiomyopathy, and dilated cardiomyopathy.

SEQUENCE LISTING FREE TEXT

SEQ ID NOS: 1-4: primer

All publications, patents, and patent applications cited herein are incorporated herein by reference in their entirety.

The invention claimed is:

1. A method for producing a myocardial sheet, comprising the following steps (a) to (c):
(a) producing Flk/DR positive cells, cardiomyocytes, endothelial cells, and mural cells from embryonic stem cells; and
(b) mixing the Flk/KDR positive cells with the cardiomyocytes, endothelial cells, and mural cells to obtain a cell mixture of FLk/KDR positive cells, cardiomyocytes, endothelial cells, and mural cells; and
(c) forming a sheet by culturing the mixed cells obtained in step (b) in a culture medium comprising VEGF in a culture vessel coated with a temperature-responsive polymer.

2. The method according to claim 1, wherein the Flk/KDR positive cells are induced by culturing embryonic stem cells on a gelatin-coated culture vessel.

3. The method according to claim 1, wherein in the step (a), the cardiomyocytes are produced by culturing the Flk/KDR positive cells in a state in which the Flk/KDR positive cells are contacted with cyclosporin A.

4. The method according to claim 1, wherein in the step (a), the endothelial cells and the mural cells are produced by culturing the Flk/KDR positive cells in a state in which the Flk/KDR positive cells are contacted with VEGF and cAMP.

5. The method according to claim 1, wherein in the step (b), the Flk/KDR positive cells are cultured for 1 to 7 days and then mixed with cardiomyocytes, endothelial cells, and mural cells.

6. The method according to claim 1, further comprising a step of laminating the sheet to at least one additional myocardial sheet produced according to the same method to form a laminated sheet.

7. The method according to claim 6, wherein the laminated sheet consists of three layers of myocardial sheets.

* * * * *